(12) United States Patent
Diercks et al.

(10) Patent No.: US 8,124,015 B2
(45) Date of Patent: Feb. 28, 2012

(54) MULTIPLEXED, MICROFLUIDIC MOLECULAR ASSAY DEVICE AND ASSAY METHOD

(75) Inventors: Alan Diercks, Seattle, WA (US); Adrian Ozinsky, Seattle, WA (US); Carl Hansen, Vancouver (CA); Alan Aderem, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 1131 days.

(21) Appl. No.: 11/346,222

(22) Filed: Feb. 3, 2006

(65) Prior Publication Data

US 2007/0183934 A1 Aug. 9, 2007

(51) Int. Cl.
*G01N 15/06* (2006.01)
(52) U.S. Cl. ............ 422/68.1; 422/82.01; 436/149; 436/518; 436/526
(58) Field of Classification Search .......... 422/100
See application file for complete search history.

(56) References Cited

U.S. PATENT DOCUMENTS

| | | | |
|---|---|---|---|
| 6,766,817 B2 | 7/2004 | da Silva | |
| 6,918,404 B2 | 7/2005 | Dias da Silva | |
| 7,066,586 B2 | 6/2006 | da Silva | |
| 7,244,398 B2 | 7/2007 | Kotary et al. | |
| 7,285,255 B2 | 10/2007 | Kadlec et al. | |
| 2004/0203174 A1* | 10/2004 | Jones et al. | 436/180 |
| 2005/0019792 A1* | 1/2005 | McBride et al. | 435/6 |
| 2006/0240416 A1* | 10/2006 | Banerjee et al. | 435/6 |
| 2007/0264634 A1* | 11/2007 | Bock et al. | 435/6 |
| 2008/0015531 A1 | 1/2008 | Hird et al. | |

FOREIGN PATENT DOCUMENTS

| | | |
|---|---|---|
| WO | WO 01/01025 | 1/2001 |
| WO | WO 02/43615 | 6/2002 |

OTHER PUBLICATIONS

Whitesides et al. "Flexible Methods for Microfluidics". 2001. Physics Today.*
Huh et al. "Microfluidics for flow cytometric analysis of cells and particles". 2005. Physiol. Meas. vol. 26. pp. R73-R98.*
E-mail from Elson da Silva dated Jul. 21, 2008.
Andersson et al., "Microfluidic devices for cellomics: a review," Sensors and Actuators B, 92:315-325 (2003).
Argarwal et al., "Magnetically-driven temperature-controlled microfluidic actuators," Proceedings of First International Workshop on Networked Sensing Systems (INSS2004), Tokyo, Japan, Jun. 2004, pp. 51-55 see http://www.unl.im.dendai.ac.jp/INSS2004/INSS2004_papers/OralPresentations/C2.pdf.
Ashkin et al., "Observation of a single-beam gradient force optical trap for dielectric particles," Opt. Lett., 11(5):288-290 (1986).
BD Biosciences, *Techniques for Immune Function Analysis Application Handbook*; 1st Ed., Chapter 10: 177-195 (2005); see <http://www.bdbiosciences.com/cgi-bin/literature/view?part_num=02-8100055-21A1rr>.
Brenner et al., "In vitro cloning of complex mixtures of DNA on microbeads: Physical separation of differentially expressed cDNAs," PNAS, 97(4):1665-1670 (2000).

(Continued)

*Primary Examiner* — Yelena G Gakh
*Assistant Examiner* — David Weisz
(74) *Attorney, Agent, or Firm* — Morrison & Foerster LLP

(57) ABSTRACT

Microfluidic systems are disclosed, including microfluidic devices and methods, useful for simultaneously analyzing multiple analytes in each of a plurality of distinct nanoliter-volume samples.

16 Claims, 13 Drawing Sheets

OTHER PUBLICATIONS

Chemican International, *Introduction to Antibodies*; 2nd Ed.; see <http://www.chemicon.com/resource/ANT101/atoc.asp>.

Chen et al., "High-Throughput DNA Analysis by Microchip Electrophoresis," *Combinatorial Chemistry & High Throughput Screening*, 7:29-43 (2004).

Carter, A.N. (1997). "Permeabilization Strategies to Study Protein Phosphorylation." Unit 18.8 in *Current Protocols in Molecular Biology*, Ausubel, F.M.; Brent, R.; Kingston, R.E.; Moore, D.D.; Seidman, J.G.; Smith, J.A.; & Struhl, K. (eds.) (1997).

Diercks et al., "Microfluidic device for the multiplexed temporal measurement of proteins secreted from live single macrophages," poster presented at the Third Annual International Symposium on Emerging Technologies and Systems Biology, Seattle, WA, Apr. 25-26, 2004.

Farfan et al., "Multiplexing Homogeneous Cell-Based Assays," *Cell Notes*, 10:15-18 (2004).

Finkel et al. "Barcoding the Microworld," *Analytical Chemistry*, 76(1):352A-359A (2004).

Fredrickson et al., "Macro-to-micro interfaces for microfluidic devices," *Lab Chip*, 4:526-533 (2004).

Han et al., "Quantum-dot-tagged microbeads for multiplexed optical coding of biomolecules," Nat. Biotechnology 19:631-635 (2001).

Kellar et al., "Multiplexed Fluorescent Bead-Based Immunoassays for Quantitation of Human Cytokines in Serum and Culture Supernatants," *Cytometry*, 45:27-36 (2001).

Liu et al., "A nanoliter rotary device for polymerase chain reaction," *Electrophoresis*, 23:1531-1536 (2002).

Matthias et al., "Monodisperse Diameter-Modulated Gold Microwires," *Advanced Materials*, 14(22):1618-1621 (2002).

Nguyen, Nam-Trung and Steven T. Werely. *Fundamentals and Applications of Microfluidics*. Boston: Artech House p. 2-5 (2002).

Nicewarner-Peña et al., "Submicrometer Metallic Barcodes," *Science*, 294:137-141 (2001).

Ouellette, "A New Wave of Microfluidic Devices," *The Industrial Physicist*, 4:14-19 (2003).

Quake et al., "From Micro- to Nanofabrication with Soft Materials," *Science*, 290:1536-1540 (2000).

Sia et al., "Microfluidic devices fabricated in poly(dimethylsiloxane) for biological studies," *Electrophoresis*, 24:3563-3576 (2003).

Tárnok et al., "Cytometric Bead Array to Measure Six Cytokines in Twenty-Five Microliters of Serum," *Clinical Chem.*, 49:1000-1002 (2003).

Thorsen et al., "Microfluidic Large-Scale Integration," *Science*, 298:580-584 (2002).

Unger et al., "Monolithic Microfabricated Valves and Pumps by Multilayer Soft Lithography," *Science*, 288:113-116 (2000).

Vandaveer et al., "Recent development in amperometric detection for microchip capillary electrophoresis," *Electrophoresis*, 23:3667-3677 (2002).

Walt D., "Bead-based Fiber-Optic Arrays," *Science*, 287:451-452 (2000).

Whiteside T.L., "Cytokine Assays," *BioTechniques*, 33:S4-S15 (2002).

Wu et al., "Establishment of ELISA on 384-Well Microplate for AFP, CEA, CA 19-9, CA 15-3, CA 125, and PSA-ACT: Higher Sensitivity and Lower Reagent Cost," *J. Clin. Lab. Anal.*, 17:241-246 (2003).

* cited by examiner

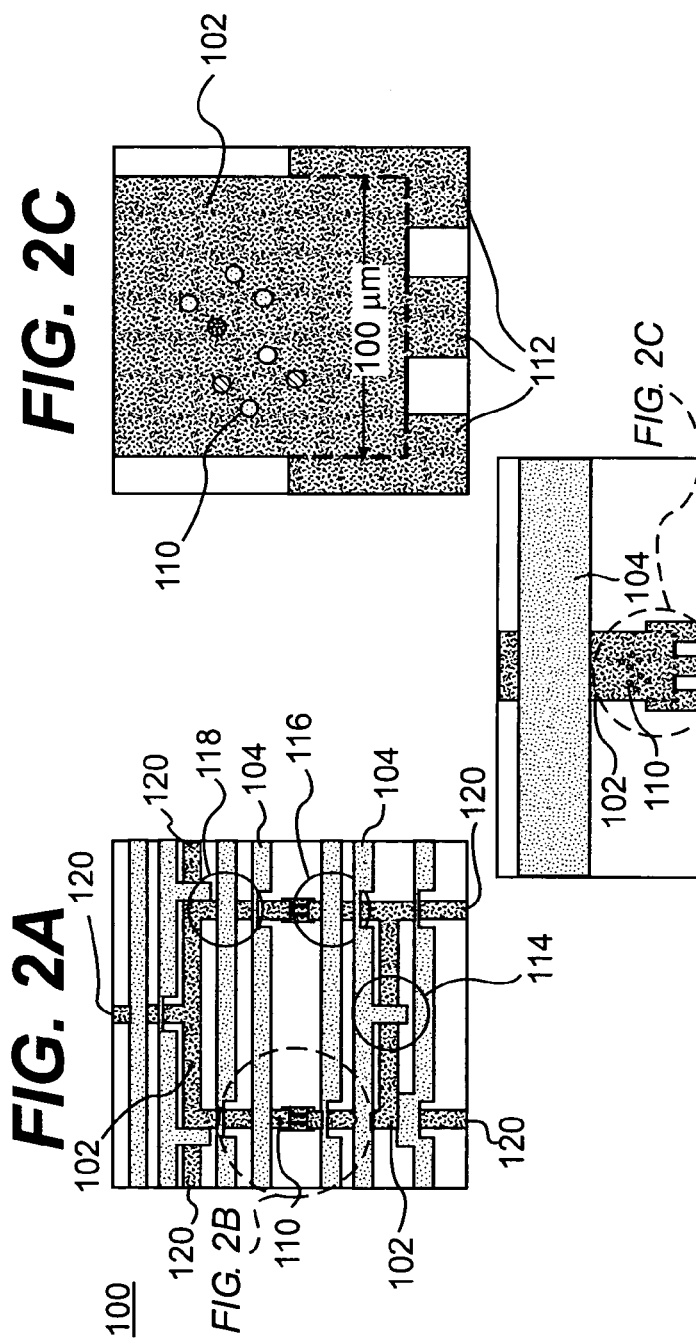
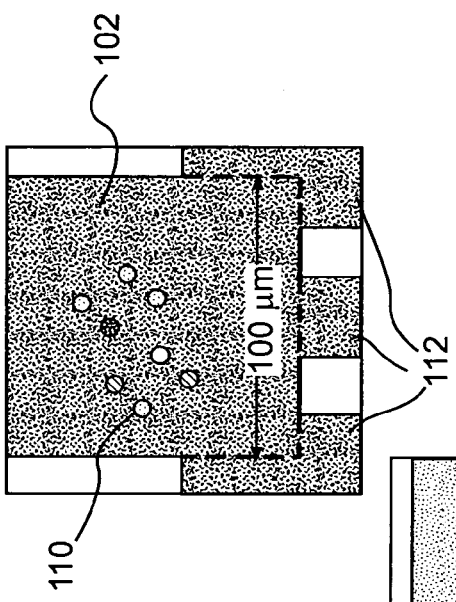
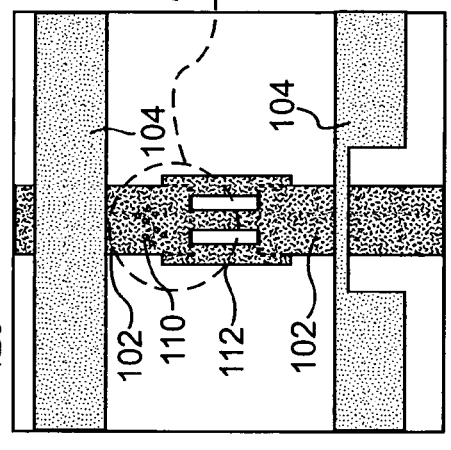

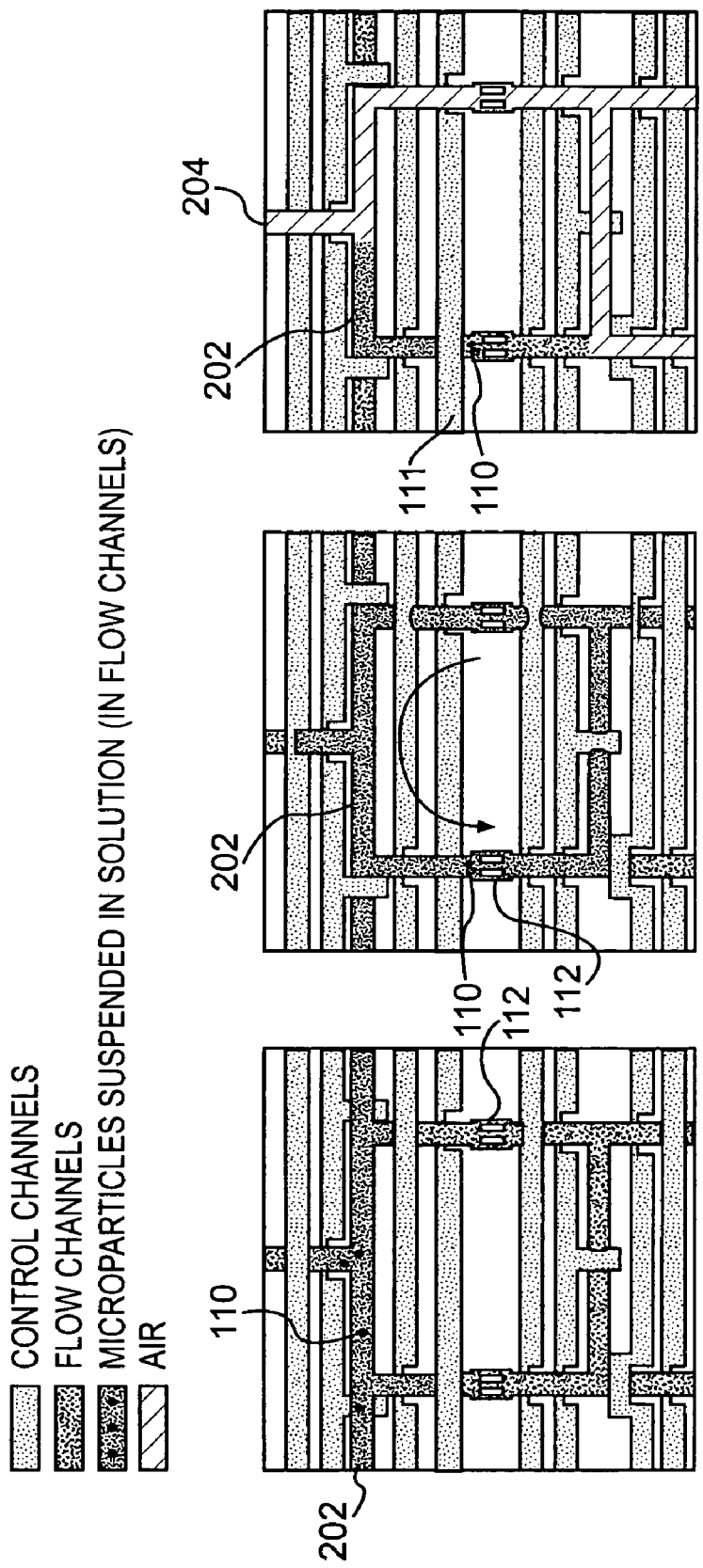

☐ SOLUTION (IN FLOW CHANNELS)
☐ SAMPLE (IN FLOW CHANNELS)
☐ WASH SOLUTION (IN FLOW CHANNELS)
☐ CONTROL CHANNELS

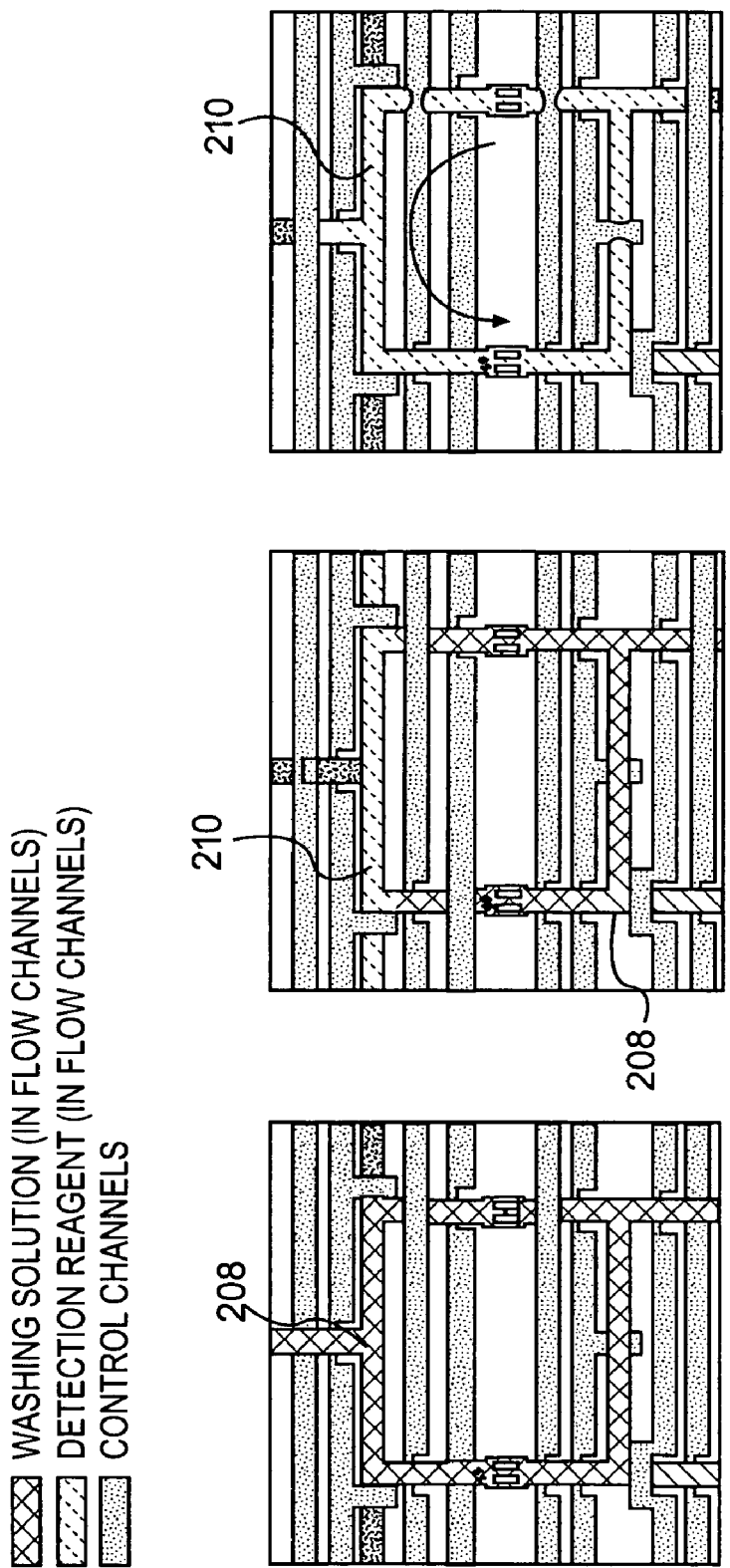

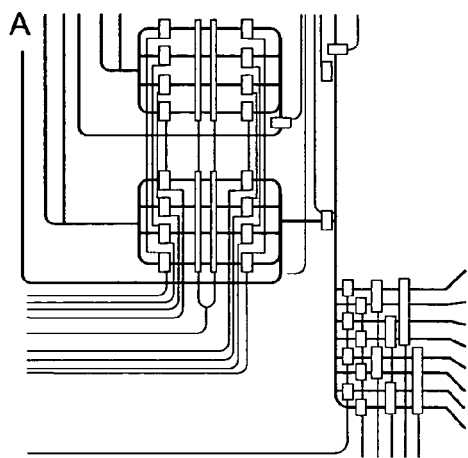 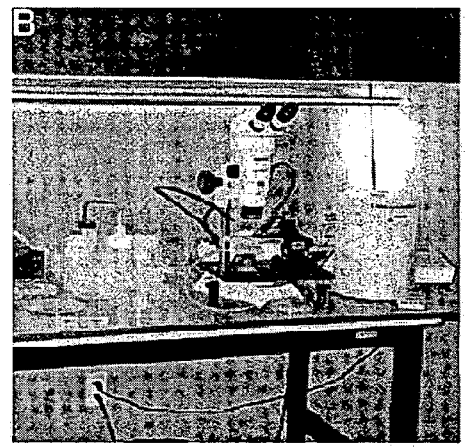
FIG. 5A  FIG. 5B
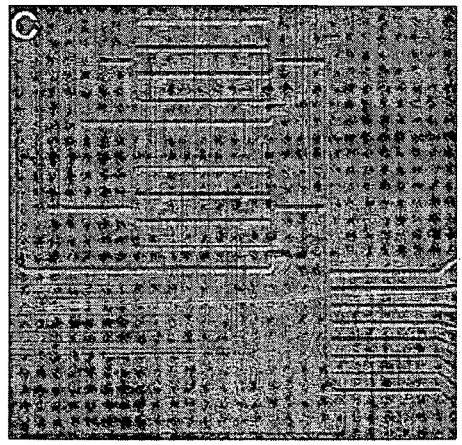 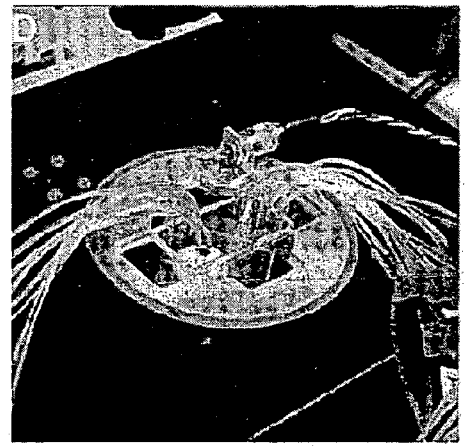
FIG. 5C  FIG. 5D

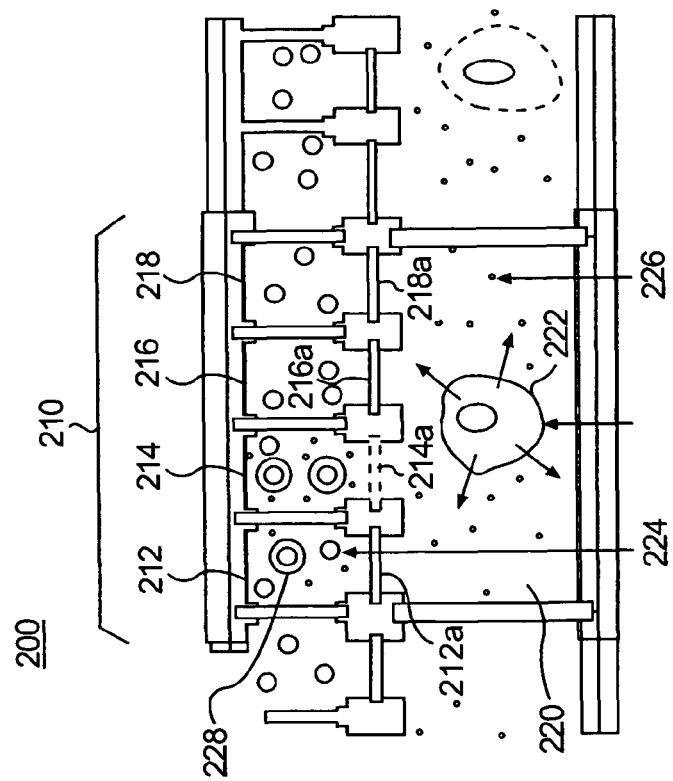
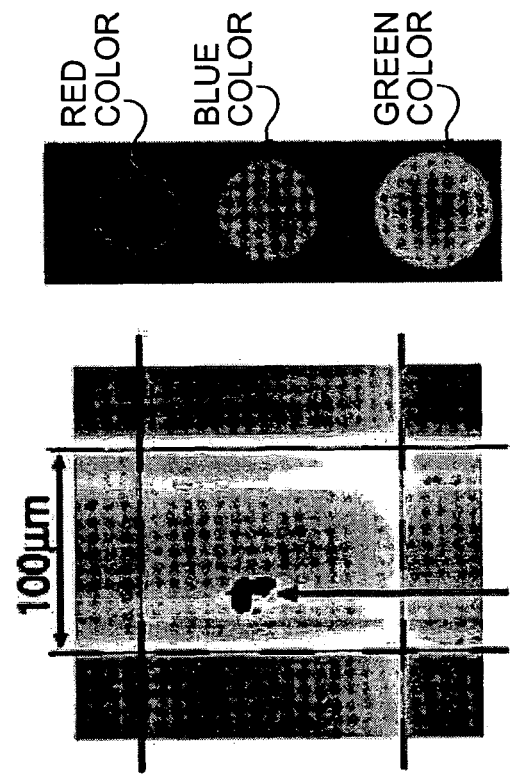
FIG. 6A   FIG. 6B   FIG. 6C

RED PARTICLES

GREEN PARTICLES

MULTIPLEXED, MICROFLUIDIC MOLECULAR ASSAY DEVICE AND ASSAY METHOD

STATEMENT OF RIGHTS

The U.S. Government may own rights in the present invention pursuant to funding of research under NIH/NIAID Grant Nos. 2 R37 AI25032, 2 R01 AI32972, and R21 AI063007.

FIELD OF THE INVENTION

The present invention is generally directed to microfluidic systems, including microfluidic devices and methods, useful for simultaneously analyzing multiple analytes in each of a plurality of distinct nanoliter-volume samples.

BACKGROUND

Multiplex Assays

Multiplexing or multiplex assay refers to the ability to send, receive, detect, separate, differentiate, or analyze multiple signals or streams of information simultaneously, from the same source. Multiplexing of assays include the ability to: conduct multiple tests (e.g., chemical assays, biological assays, immunosorbent assays, immuno-assays, and the like); measure or detect multiple items (e.g., antigen concentration, antibody concentration, analytes such as cytokines, chemokines, inflammatory mediators, and their receptors that are present in biological fluids (e.g. serum, plasma, urine, tear, cell culture supernatants, intact cells or their lysates), functionalized microspheres, eTags, labeled moieties, and the like); or manipulate multiple items (e.g., animal cells, bacteria, viruses, their culture supernatants, enzymes, macromolecules, or their mixtures) individually, at the same time, or within the same sample, or within the same test tube/chamber/well/compartment.

Examples of current multiplex biological assays include DNA microarrays (used, for example, for gene expression profiling or for the detection of nucleotide sequence mutations or deletions); assays in combinatorial chemistry (for the analysis of multiple closely-related chemical compounds); and immunology-based assays (such as the Enzyme-Linked Immunosorbent Assay (ELISA) used to detect and quantify antigens), among others.

Existing multiplex assays are generally limited by the number of analytes they can simultaneously detect or differentiate. In the following text, some characteristics of current multiplex assay systems will be discussed in the context of ELISA systems, which embody many of the characteristics shared by most existing biological multiplex systems. Current multiplexing systems, such as standard ELISA, allow for the quantitation of one analyte per each well of sample. Typically, in these systems, a sample is divided among several wells of a microplate. Currently, 96-well ELISA plates are commonly used and require up to 100 µL of sample per well or up to 9.6 mL of sample per plate. The 384-well and 1536-well ELISA plates are also becoming available. These plates require a smaller volume of sample per well than 96-well plates, however, a relatively large volume of sample is still needed per plate. See, for example, Wu et al. *J. Clin. Lab. Anal.* 17:241-246 (2003). One drawback of standard multiplex assays is that they require a relatively large amount of sample to measure more than one analyte. Another drawback is that liquid handling becomes a problem for microplate-based assays with a higher number of wells. Usually, sophisticated and expensive liquid handling systems must be used to dispense and wash samples in these plates.

To scale down the amount of sample needed for multiplex assays, multiplex fluorescent bead-based immunoassays have been developed that allow the measurement of several proteins in a single sample well. These systems utilize a combination of several fluorescently-distinguishable microsphere beads, each covalently coupled to an antibody that can specifically capture a particular type of protein within the sample. Normally, a handful of specific capture beads are mixed with a minimum volume of the sample (in the microliter range) in each well of a 96- or higher number-well microplate. Each microsphere bead can act as an independent solid surface to which a specific analyte can be attached and be subsequently detected. See, for example, Kellar et al., *Cytometry* 45:27-36 (2001). A major drawback of these systems is again the need for a relatively large volume of sample and reagent per microplate for detecting a handful of analytes. Thus, these assays can be costly, and at times unsuitable for those instances where there is only a very small quantity of sample available. A further drawback is the liquid handling problem that arises when using 384- or higher number-well ELISA microplates. Liquid handling and sample evaporation become major problems when dealing with small volumes of samples in an open system. An additional drawback of the current multiplex ELISA systems, which also applies to standard ELISA assays, is the possibility for contamination and cross-contamination of samples since plates are open to the environment.

Yet another limitation of existing multiplex systems is that, due to relatively large microliter-scale volume of sample used per well, each analyte must be assayed with multiple beads of the same type to prevent signal saturation. Similar beads will compete with each other to bind to the same analyte. This situation decreases the sensitivity of the assay because the target analyte present in the sample is distributed over all of the beads specific for that analyte; and each bead will be reporting only a fraction of the analyte concentration. The mean value of the analyte concentration will, therefore, have a large standard error due to variable concentration values reported by each bead.

As a standard operating protocol, microplates in microplate-based assays are vortexed or rocked at room temperature for an extended period of time to allow the analytes to be mixed well with functionalized microbeads in each well. The drawback of such a mixing procedure is that it could lead to sample evaporation, spilling, cross-contamination, and analyte degradation.

A further limitation with existing multiplex systems is that they test samples that come from tissue culture supernatants or biological fluids that contain analytes produced by mixed cell populations. The current multiplexing systems cannot provide direct information about the analyte profiles of individual cells or if they do their level of multiplexing is very limited. Another drawback of the current multiplex systems is that they are unable to detect expression kinetics of different analytes instantaneously as they become expressed or secreted (e.g., when analytes are secreted from a live cell). Currently, in order to study, for example, the kinetics of cytokine expression in cells after a particular treatment, culture supernatants must be collected at various time points after the treatment and be frozen and saved until samples from all time points are gathered. Subsequently, samples are thawed out and applied to multi-well plates for studying cytokine expressions over time. A major drawback of such a procedure is that it fails to properly quantify any analyte that is short lived or is degraded as the result of lengthy experimental procedures, improper laboratory handling, freeze-thawing, and the like.

Consequently, to alleviate the shortcomings of current multiplexing systems, there is a need for devices and methods capable of detecting multiple analytes in a single sample using sub-microliter volumes, thereby reducing the cost and the need for large volume of samples and reagents. There is also a need to automate the liquid handling and the assaying procedures to reduce costly laboratory time and effort required to perform larger-scale assays. There is a further need for assays to be performed in an enclosed environment so that sample evaporation, spilling, contamination, and cross-contamination are eliminated. There is also a need for a system that can detect the analyte profile at a single-cell level. There is a further need for a single-cell system to be capable of capturing analytes as they are secreted from the cell. Moreover, there is a need for a single-cell assay to be capable of sampling analytes at several time intervals so that the kinetics of analyte expression or secretion from the cell can be measured over time.

The devices and methods of the present invention provide the tools to accomplish these objectives by using microfluidic systems.

Microfluidic Systems

Microfluidics refers to a set of technologies that control the flow of nanoliter and picoliter amounts of fluids in miniaturized systems.

It is not generally possible to scale down existing assaying methods and devices and expect them to work in microfluidics applications. One problem encountered is that the behavior of a fluid changes dramatically at the micron scale. For example, capillary action can have an effect on how fluids pass through microscale-diameter tubes. Additionally, other factors, such as heat transfer and mass transfer, can have a different effect in micro-scale systems, as compared to macroscale systems. Another problem associated with the scale down of existing assaying methods is that fluid viscosity dominates over momentum, thus resulting in, among other things, problems with mixing.

The advent of "multilayer soft lithography" (MSL) techniques and multilayer microfluidic systems made by it, however, have solved some of the problems mentioned above in the field of microfluidics. In MSL, multilayer structures are constructed by binding multiple patterned layers of elastomers. In such structures, the fluid flow in microfluidic channels of one layer (the control layer) provides an actuation force necessary to control the fluid flow in another layer (the flow layer). As a result, the active multilayer microfluidic devices produced by MSL techniques can have multiple valves and pumps completely made out of elastomers. Such multilayer microfluidic devices are superior to microelectromechanical structures (MEMS) in that they are not limited by the common problems associated with moving liquid by techniques such as electroosmotic flow or dielectrophoresis. See, for example, Unger et al., *Science* 288:113-116 (2000).

Existing MEMS microfluidic systems and technologies have found utility in ink-jet print heads, fabrication of DNA microarrays, and DNA analysis technologies, among a myriad of other applications. See, for example, Chen et al., *Combinatorial Chemistry & High Throughput Screening* 7(1):29-43 (2004). These systems and technologies, however, employ complicated fabrication techniques, and utilize fragile and expensive components. Moreover, many of these systems are only adapted to a single type of experiment, technique, or use.

Accordingly, the present invention eliminates the limitations of current multiplex assays by providing MSL-based microfluidic devices and methods that can replace macroscopic laboratory tools with smaller, automated, and more efficient tools that are adaptable to more than one experiment, technique, or use. The present invention further provides low cost, quantitative, microfluidic assaying methods and devices adaptable to biotechnological, biological, biomedical, pharmaceutical, chemical, or environmental uses, among others. The present invention provides a straightforward solution to the challenge of measuring multiple analytes within each chamber within closed microfluidic devices.

BRIEF SUMMARY OF THE INVENTION

The present invention is generally directed to microfluidic systems, including devices and methods, useful for simultaneously analyzing multiple analytes from each of a plurality of distinct nanoliter-volume samples.

In an embodiment, the present invention is directed to a microfluidic device comprising: one or more sample chambers; wherein at least one of the one or more sample chambers comprises a sample and one or more micro-scale sensing elements; wherein the volume each sample is a nanoliter volume. In one embodiment, the micro-scale sensing elements are microparticles. In another embodiment, the device contains between 1 and 10,000 sample chambers and each of the sample chambers contains between 1 and 1000 microparticles.

In another embodiment, a microfluidic device of the invention has one or more flow layers and one or more control layers. In another embodiment, the microfluidic device contains between 1 and 100 sample chambers and each of the sample chambers contains between 1 and 50 microparticles. One of the advantages of the devices of the invention is that they provide a suitable enclosed environment that eliminates the possibility for spilling, contamination, or cross-contamination of samples.

In another embodiment of the present invention, the device has one flow layer and one control layer, wherein the flow layer and the control layer are fluidically independent of each other. The flow layer can have a plurality of flow channels, and the control layer can have a plurality of control channels that cross over the flow channels to define valves. Each of the channels in each of the layers can be individually addressable, so that flow through each channel can be individually controlled. The control layer can be designed to sit on top, bottom, or on both sides of the flow layer so that when a control channel is pressurized and deflected outwards, the flow in the associated flow channel in the contiguous flow layer is affected. Pressurizing a control channel can exert external pressure on a flow channel and provide a driving force to propel fluid through the flow channel in a certain direction, it can also stop or slow the fluid flow, or it can partition the flow channel into two or more separate sections. The present invention also contemplates devices where more than one flow layer and/or more than one control layers are present. In another embodiment of the invention, channels from different layers are interconnected and provide fluid flow between two or more layers. Various configurations may be devised to move a fluid through flow and control channels. Such configurations may utilize external pressure, or electrical, electrokinetic, thermal, or other driving forces to move fluids through micro-channels. For example, a configuration may utilize an electrical driving force by configuring the electrodes and selecting the fluids so that the fluids move by electrocapillarity, electrowetting, or continuous electrowetting. Another configuration may utilize an electrokinetic force such as electrophoresis or electroosmosis. Another configuration may utilize driving forces such as dielectrophoresis, electro-hydrodynamic pumping, or magneto-hydrodynamic pumping, by configuring the electrodes and selecting and placing the fluids within the channel in an appropriate manner.

The present invention provides for suitable partitioning of a flow channel, or a series of flow channels, to create a sample chamber, which can house the sample to be analyzed. In its most simple form, a sample chamber can be an isolated section of a flow channel. However, a sample chamber can also be formed by a series of flow channels arranged in such a manner so as to form a closed loop through which the sample can be recirculated. In another embodiment of the invention, chambers can also be formed as an isolated segment of a flow channel having multiple input and output channels. A chamber can be further subdivided into one or more smaller chambers.

In another embodiment, one or more flow channels can have one or more constrictions. Such constrictions are dimensioned so that they allow the passage of fluid through the flow channel, but impede the passage of other materials whose retention is desired, such as micro-scale sensing elements (e.g., microparticles) or cells. See, for example, FIG. 2. Effectively, these constrictions trap said materials in a section of a flow channel, while allowing fluid flow around them. In this manner, microparticles can be distributed and retained in one or more different sections of one or more different flow channels throughout the flow layer of the microfluidic device.

In another embodiment of the invention, the microparticles are trapped by partial closing of valves (i.e., using control channels) in the control layer. Materials can be retained in a flow channel by using "sieves", which may be dynamic and under the control of valves in the control layer. For example, when pressurized, small footprint valves in the control layer can partially restrict the flow in the corresponding flow layer, trapping the desired materials. The present invention also contemplates other methods of trapping materials in a flow channel, such as dielectrophoresis, optical tweezers, magnets, micro wells, gels, etc.

In one embodiment of the invention, micro-scale sensing elements are used to carry out multiplex assays. A typical embodiment of a micro-scale sensing element is exemplified by a microparticle. Each microparticle is chemically functionalized with a specific reagent designed to bind a biological target molecule of interest. Examples of microparticles include microspheres made of plastic, glass, or other suitable material that can be optically distinguished by some imbedded fluorescent or luminescent material. Other examples of microparticles include those that can be distinguished by their size, shape, or light scattering properties such as metallic nanoparticles, semiconducting nanowires, aluminum-etched nanowires, shape-modulated gold wires, and the like. See, e.g., Finkel et al. *Analytical Chemistry* 76(19):352A-359A (2004).

Because microparticles are small enough to be able to flow inside a flow channel, the microfluidic plumbing network of channels and valves can be used to introduce these microparticles either selectively, or uniformly, with approximately the same proportion or in different proportions into one or more sample chambers in the microfluidic device. In one embodiment of the invention, the sample and the microparticles are introduced into the microfluidic device using the same set of flow channels. In another embodiment, the flow channels used to introduce the sample are different from the flow channels used to introduce the microparticles.

During delivery, trapping of microparticles typically occurs in sections of flow channels that are part of sample chambers, so that the analytes present in the sample can interact with the microparticles. However, another embodiment of the present invention also contemplates the use of sample chambers that themselves do not contain microparticles, but which connect to adjacent detection chambers that do contain microparticles. In this setup, the solution in the sample chamber can be allowed to contact microparticles in each of the neighboring detection chambers in a time-dependent manner by opening and closing the valves that separate the sample chamber from the detection chambers.

In a particular embodiment of the invention, the microfluidic device comprises between 1 and 10,000 fluidically-isolatable sample chambers; wherein each of said one or more sample chambers contains between 1 and 1,000 different types of microparticles, each type of microparticle being capable of binding to a different or the same analyte. In another embodiment of the invention, the microfluidic device comprises between 1 and 1000 fluidically-isolatable sample chambers; wherein each of said one or more sample chambers contains between 1 and 100 different types of microparticles, each type of microparticle being capable of binding to a different or the same analyte. Still, in another embodiment of the invention, the microfluidic device comprises between 1 and 100 fluidically-isolatable sample chambers; wherein each of said one or more sample chambers contain between 1 and 50 different types of microparticles, each type of microparticle being capable of binding to a different or the same analyte. Other microfluidic devices of the invention may contain between 1 and 10 fluidically-isolatable sample chambers. It should be understood however, that these numbers are not limiting and that a device within the scope of the invention can be made following the teachings of the present invention comprising a higher number of fluidically-isolatable chambers and/or different types of microparticles.

Once microparticles have been distributed among the sample chambers in the microfluidic device, the plumbing network of channels and valves can be used to introduce the sample into the plurality of sample chambers in the microfluidic device. The sample can then interact with the functionalized microparticles in a detection chamber by diffusive mixing. However, in another embodiment, the contacting of the sample with the microparticles can be further improved by recirculation of the sample over the microparticles. Recirculation enables thorough interaction of the samples with the microparticles, thereby increasing capture efficiency and detection sensitivity. Recirculation can be carried out by using rotary mixers, by suitable application of external pressure to one or more flow channels (e.g., by fully or partially closing and opening flow channels in a sample chamber; see also FIG. 3), or by any other method known in the art that allows movement of flow in microfluidic channels.

Although typically the microparticles are introduced into the microfluidic device first, followed by the sample, the present invention also contemplates methods wherein these steps are reversed or wherein a combination of different sequence steps is used to achieve a final setup wherein microparticles and samples are placed in contact with each other.

The microfluidic plumbing network of channels and valves can also be used to introduce appropriate buffers and reagents (e.g., blocking solutions, hybridization solutions, wash buffers, detection antibodies, secondary antibodies, fluorescent dyes, etc.) into the device in order to render the microparticles detectable by a number of different detection strategies. A typical detection technique when using optically-distinguishable microparticles includes the use of a light/fluorescent microscope.

The methods and techniques described above can be summarized in another embodiment of the invention directed to a method for analyzing one or more analytes in each of one or more nanoliter volume samples simultaneously. Accordingly, said method comprises:

optionally introducing into each of said one or more sample chambers and flow channels going into, or exiting, said one or more sample chambers, any reagents (e.g., blocking reagent, wash buffer, etc.) useful in pre-treating the active area of the chip, introducing one or more micro-scale sensing elements, each capable of binding a different or the same analyte, into each of one or more sample chambers of a microfluidic device of the invention;

introducing one or more samples, each comprising one or more analytes, into each of said one or more sample chambers so that each sample is placed in contact with a separate set of said one or more micro-scale sensing elements;

optionally introducing into each of said one or more sample chambers any reagents necessary to obtain a detectable signal from said one or more same or different types of micro-scale sensing elements;

detecting a signal from said one or more same or different types of micro-scale sensing elements; and interpreting the signal to obtain the desired information about said one or more analytes. In one embodiment of the invention, the presence of an analyte can be detected, the analyte can be identified qualitatively, or its amount, concentration, or activity can be measured quantitatively.

In another embodiment of the invention, the cellular, intracellular or the secreted biological target molecules from one or more cells inside the sample chamber are sequentially circulated over or allowed to come into contact with microparticles in one of many detection chambers while isolated from all other detection chambers. See, e.g., FIG. 6. For instance, the secreted biological molecules (i.e., the sample) are placed in contact with the microparticles in the first detection chamber at time 1. At time 2, with detection chamber 1 now closed, the sample is circulated over or allowed to come into contact with microparticles in detection chamber 2. At time 3, and with detection chamber 1 and 2 now closed, the sample interacts with microparticles in the third detection chamber. This process can continue depending on the number of detection chambers present in each of the flow channels. The detection can occur after or during one or more time points during which the biological target molecules were allowed to come into contact with partitioned microparticles.

In another embodiment, the present invention provides a microfluidic device and method for recovering and sorting of cells from the device based on analyte expression profiles or properties of the cells.

In another embodiment, the present invention provides a microfluidic device and method where the operation of an experiment is altered based on initial information obtained from a sample. For example, cells in sample chambers can be treated with different reagents to determine how they respond to various stimulants. Based on the initial response, the cell(s) can be subjected to a different set of conditions that will interrogate behavior under different parameters. In another example, the device may be used to assay for a general set of cytokines for both types of helper T cells (Th1 and Th2) (e.g., IL-4, IL-10, etc. for Th2 and IL-12, IFNg, etc. for Th1) in the host lymphocytes. Once, the initial cytokine expression profile indicates, for instance, that cells are expressing a Th1 response, the operation of the device may be altered in such a way that subsequent assays become focused on Th1 cytokines (i.e., any cytokine in Th1 signaling pathway) and not Th2 cytokines. The same scenario can be envisioned for disease markers. Once an assay is performed for a general set of disease markers, the protocol can be altered to assay for a specific set of markers pertaining to a specific disease or condition.

In another example, the operation of the device of the invention may be altered if signal saturation is present. For instance, if it is detected that the probing microparticle(s) for a specific cytokine in a given chamber is saturated with a target analyte, more microparticles of the same kind can be added to a different sample chamber and the sample can be distributed over these microparticles removing the saturation effect.

In another embodiment, an increasing amount of microparticles (either of a single kind or of a different kind) can be added to sequential sample chambers so that even if microparticle saturation occurs in sample chambers with relatively few microparticles, the analysis of analytes in a sample can nonetheless be accomplished without saturation in sample chambers with the appropriate number of microparticles.

Because of the magnitude of the sample volume needed in the instant microfluidic devices, the multiplexing methods of the invention provide a significant reduction in assay reagents usage when compared to existing assays that use, for example, 96-well microplates. Moreover, the throughput gain of the multiplexing methods and devices of the invention can be from 10 to 1000-fold, when compared to existing multiplexing assays. For example, existing 96-well plate-based assays use about 100 μL/well of both sample and reagents to measure one species of target molecule. An embodiment of the present invention, however, utilizes samples in the nanoliter volume range and correspondingly smaller amounts of associated reagents for the same assay. A single 96-well plate-based assays using 100 μL/well of sample would require a total of about 9,600 μL of sample. In accordance with an embodiment of the present invention, this volume would be enough to run 9,600,000 one-nanoliter assays.

DESCRIPTION OF THE DRAWINGS

In the following description, reference is made to the accompanying drawings that form a part thereof. These drawings and accompanying description illustrate specific exemplary embodiments. These embodiments are described in sufficient detail to enable those skilled in the art to practice the invention. It is to be understood, however, that other embodiments can be utilized and that changes can be made without departing from the scope of the present invention.

The flow channels 16 are typically 15 μm high and 100 μm wide, but other dimensions can also be used as long as suitable flow of fluids is achieved. As mentioned previously, the device can also employ narrower channels to constrict the flow and trap materials such as microspheres or cells in the chambers. Dimensions of exemplary narrower channels include 4 µm high and 40 µm wide. In FIG. 1, the distance W is 25.4 mm.

FIGS. 2A-C show exemplary schematic representations of a single microfluidic chamber showing detailed views of a portion of the device shown in FIG. 1. FIG. 2A shows a schematic illustration of a single assay chamber 100 in accordance with an embodiment of the present invention. The flow layer channels 102 carry the sample and all of the reagents used in the assay. The control layer channels 104 operate as valves on a separate layer that when pressurized seal one or more of the flow layer channels 102. FIG. 2A includes five input ports 120 that provide sample and reagent flow in and out of the re-circulating chamber 100. By activating the three circled valves 114, 116, and 118 in sequence, fluid can be recirculated around the chamber 100. FIG. 2B shows a schematic illustration of an expanded view depicting trapped microspheres 110. The flow channel 102 contains a set of constrictions 112, which are small enough in diameter to trap the microspheres 110, while still allowing fluid to pass.

FIG. 2C shows a schematic representation of a detailed view depicting multiple optically distinguishable microspheres 110 trapped by the channel constrictions 112. In the example shown, the microspheres 110 are approximately 5.6 µm in diameter while the flow channel 102 is 15 µm high and the constrictions 112 are 4 µm high.

FIGS. 3A to 3I show a schematic representation of the steps used to perform an assay in a microfluidic device according to the present invention. In FIG. 3A, a suspension 202 of optically distinguishable microspheres 110 is introduced into one arm of the recirculating chamber. In FIG. 3B, recirculation is activated and the beads 110 are pushed up against the constrictions 112. In FIG. 3C, the microspheres are trapped in place using valve 111. The right side of the chamber is evacuated by pushing a fluid (e.g., air) 204 into the channel. In FIG. 3D, the sample 206 is introduced into the right side of the channel. In FIG. 3E, the pump is activated and the sample is recirculated over the trapped microparticles 110. In FIGS. 3F and 3G, excess sample is flushed from the chamber with a washing solution 208. In FIG. 3H, fluorescently labeled detection reagent 210 is introduced into one arm of the recirculating chamber. In FIG. 3I, the detection reagent 210 is recirculated over the microparticles 110 in order to detect the bound target material from the sample. The microfluidic plumbing is used to flush and introduce various reagents into the microfluidic device that, by contacting the biological target molecules bound to the optically encoded particles, cause an optical signal that is characteristic of the abundance, level, or presence of biological target molecule captured on the functionalized particles.

Figure 1:
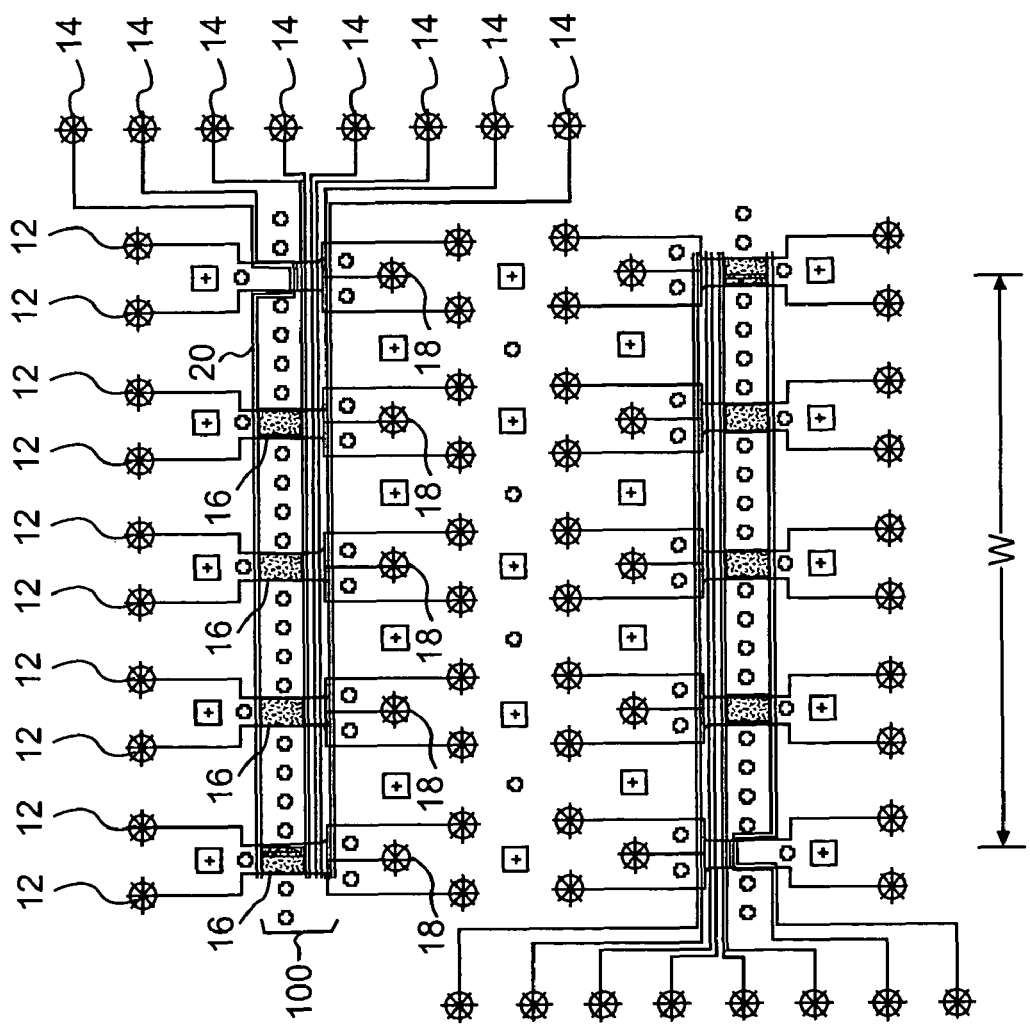
FIG. 1 shows a schematic representation of an exemplary microfluidic device 10 in accordance with an embodiment of the present invention. The microfluidic device 10 includes ten assay chambers 100 that are in fluidic communication with fluidic input ports 12. The fluidic input ports 12 are used to introduce a sample and reagents into the microfluidic device 10. The control ports 14 connect pressurized fluid to the control channels 20, which are formed as dead-end channels and deflect downward when pressurized to seal the flow channels 16. Reagents and sample flowing out of the assay chambers 100 are collected at fluidic outlet ports 18.

Control layer connections 44 (with operating pressure of 7-15 psi) connect the control layer 56 to a pressurized fluid source (not shown) supplying fluid at a pressure ranging from about 0 psi to 5 psi. In this example, the control layer 56 is 3 mm thick using 5:1 PDMS.

The flow layer 54 and control layer 56 are formed on a glass substrate 52, which is approximately 0.17 mm to 1 mm thick.

The microfluidic system 40 also comprises a heating system comprising electrodes 48 and an ITO coating 50. The ITO coating 50 ranges from 30 to 60 Ohms/sq. The microfluidic system 40 also comprises a RTD temperature sensor 46. In one embodiment, the heating current is 100 mA at a potential of 10V.

FIGS. 5A-D show exemplary schematic representations depicting various steps employed in fabricating and using a microfluidic device. FIG. 5A shows a computer aided design of channels in a microfluidic device. The computer aided design is used as a guide for creating molded PDMS elastomer layers that form channels, chambers, valves, pumps, etc. As depicted in FIG. 5B, a microscope is employed in the PDMS molding and multilayer alignment steps. The completed device is subsequently bonded to a glass substrate (FIG. 5C), and mounted on a confocal microscope (FIG. 5D). Tubing lines used for pneumatic valve control and reagent delivery are connected to the microfluidic device. It is also possible to add integrated temperature control system to the microfluidic device for live cell work. Typically this is done by applying resistive heating to the glass substrate.

FIGS. 6A-C show exemplary schematic representations depicting a microfluidic device for multiplexed single-cell assays. FIG. 6A depicts a design of a multiplexed assay device used for detecting cytokines secreted from a single live macrophage at different time intervals; FIG. 6B shows capture beads in a microfluidic device, channel margins are indicated; FIG. 6C depicts images of a single red/blue coded bead, with detection of captured MIP-2 cytokine (green).

Figure 7A:
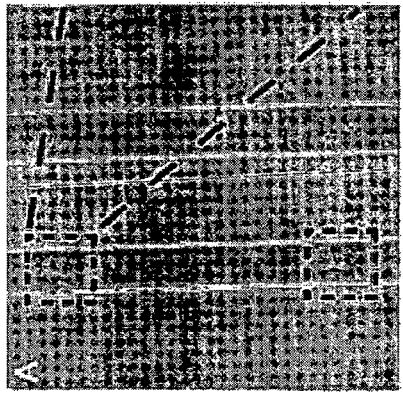
Figure 7B:
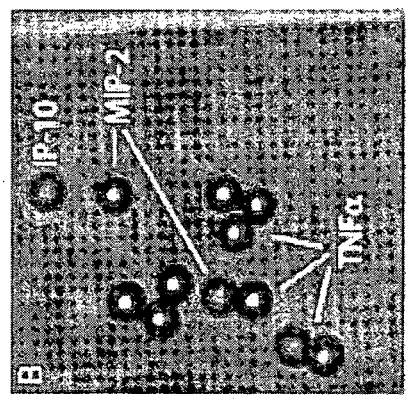
Figure 7C:
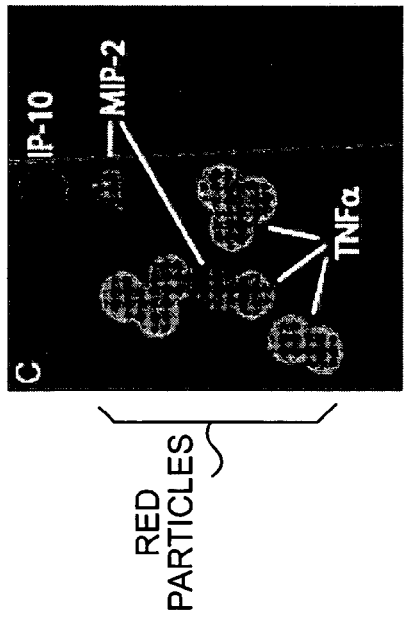
Figure 7D:
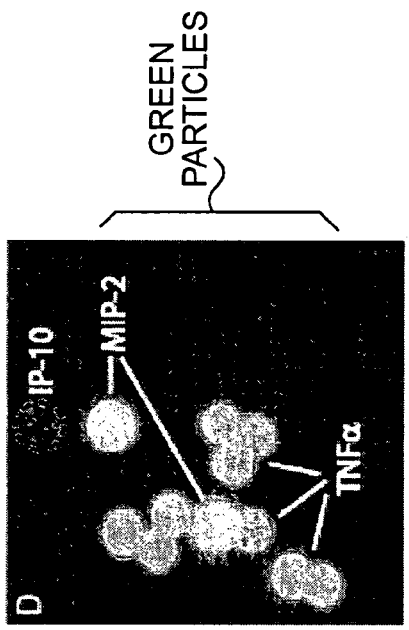

FIGS. 7A-D show exemplary schematic illustrations depicting multiplexed microparticle-based detection of cytokines using three different types of microparticles (MIP-2, TNF-α and IP-10) trapped in a sample chamber. FIG. 7A shows a transmitted light image of the microparticles showing all structures present in the chamber. FIG. 7B, is a close-up image of the microparticles shown in FIG. 7A. FIG. 7C shows that the three types of microparticles can be distinguished by their level of coding red fluorescence. In this case, the TNF-α microparticles are brighter than the MIP-2 microparticles. In FIG. 7D, the green intensity indicates the amount of each cytokine captured on the microparticles. For example, a higher concentration of MIP-2 was detected compared to TNF-α. In this sample, IP-10 is not present.

Figure 8A:
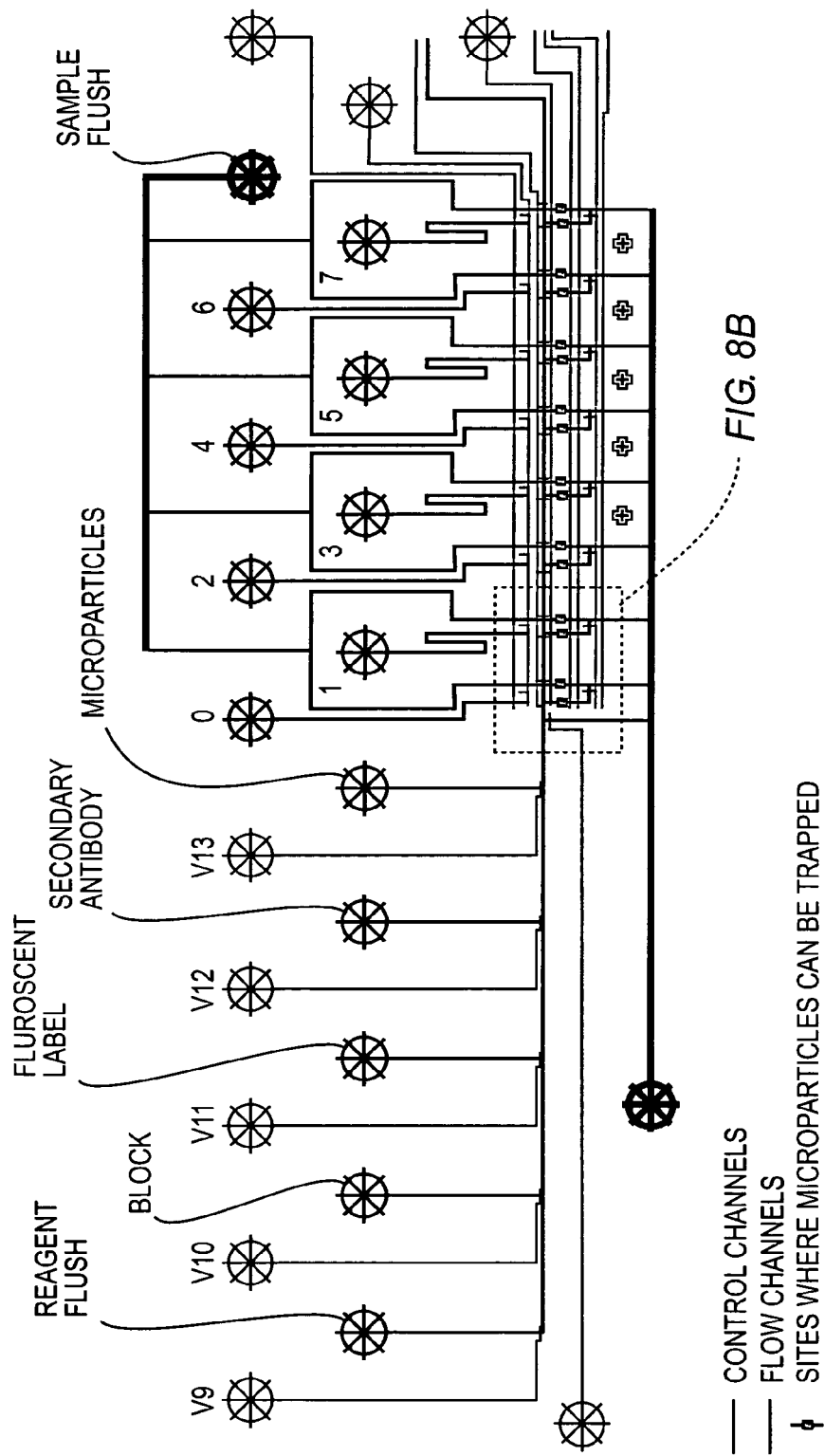
Figure 8B:
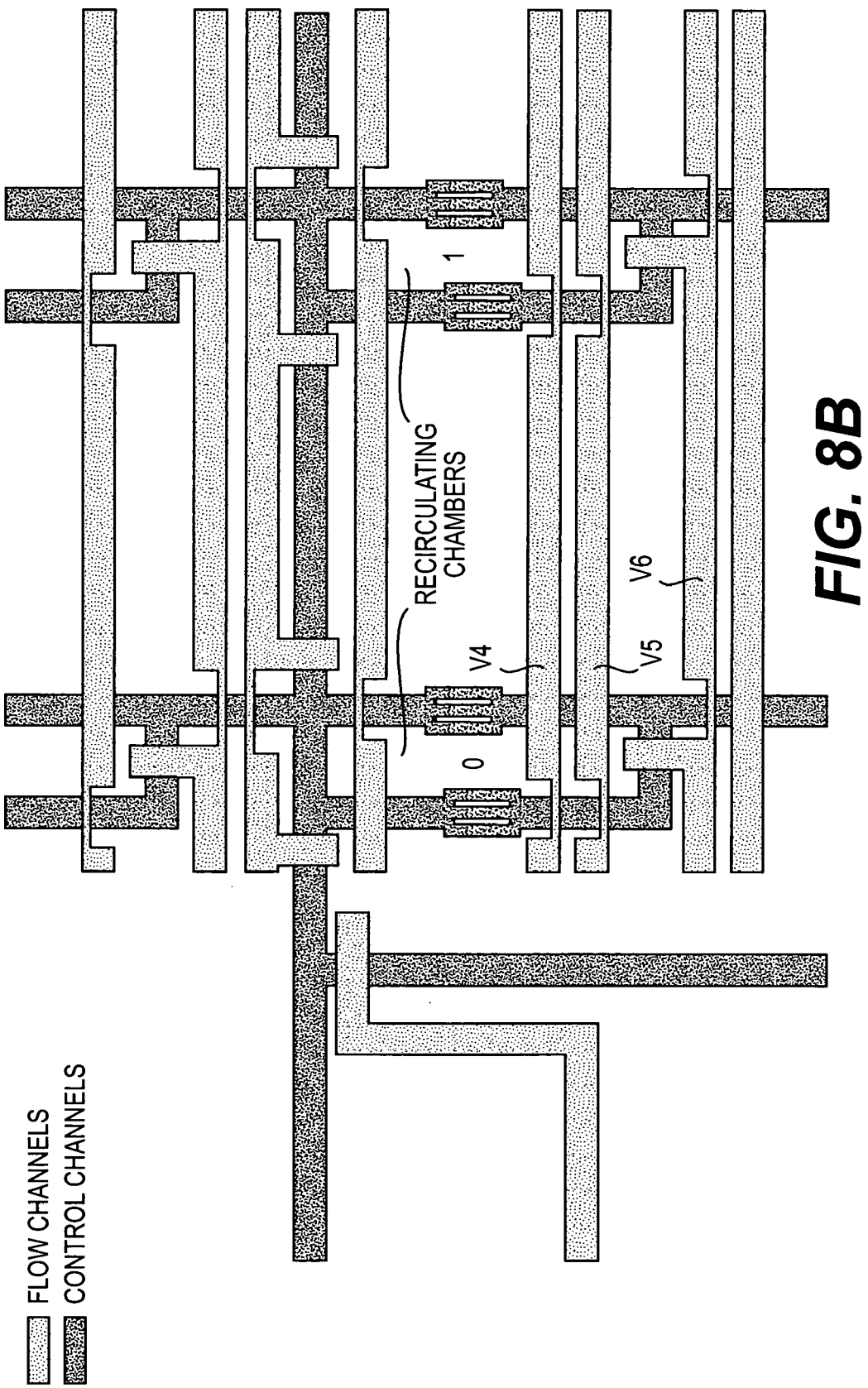

FIGS. 8A-B show an exemplary schematic representation of an microfluidic device in accordance with an embodiment of the present invention. The microfluidic device in FIG. 8A includes 8 assay chambers that are in fluidic communication with various fluidic input ports (i.e., sample input ports 0-7; as well as ports for reagent flush; blocking solution; fluorescent label solution; secondary antibody solution; and microparticles.) Control-layer channels are shown in thin black lines while flow-layer channels are shown in thicker black lines. The control ports connect pressurized fluid to the control channels, which are formed as dead-end channels and act as valves where appropriate. Sample flush port is used to simultaneously introduce wash buffer into the recirculating loop of the eight assay chambers of FIG. 8A. FIG. 8B is a close-up view of two of the assay chambers of FIG. 8A. As shown in this figure, the control layer channels operate as valves on a separate layer, that when pressurized, seal one or more flow layer channels and cause the reagent flow to re-circulate around each assay chamber in a specific direction, as explained, for example, in FIG. 2A.

Figure 9A:
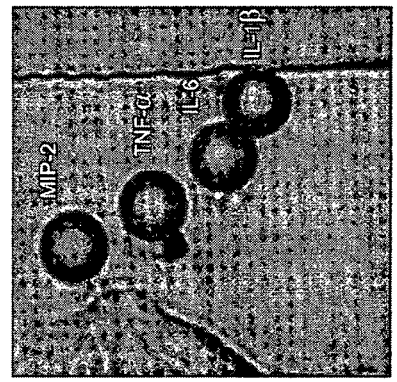
Figure 9B:
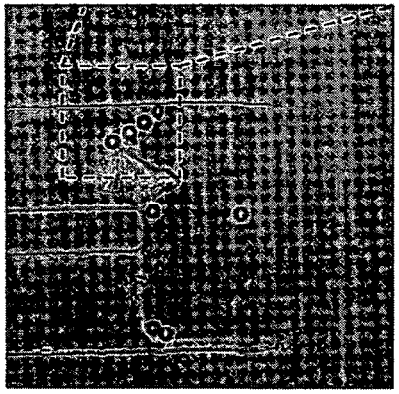
Figure 9E:
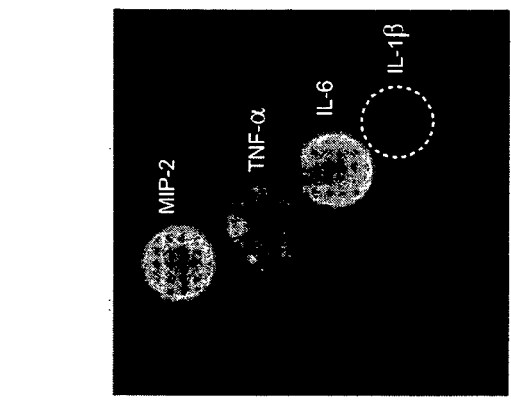
Figure 9D:
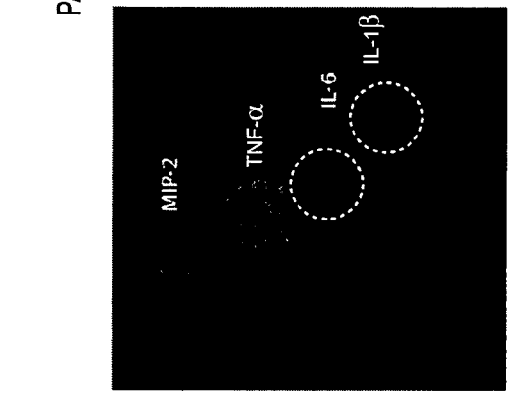
Figure 9C:
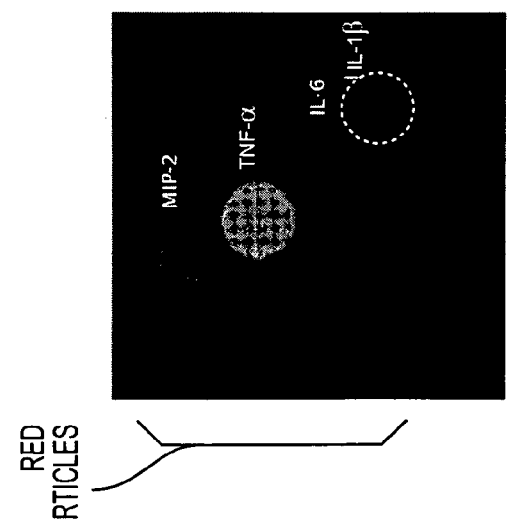

FIGS. 9A-E show exemplary schematic illustrations depicting multiplexed microparticle-based detection of cytokines using four different types of microparticles (IL-6, MIP-2, TNF-α, and IL-1β) trapped by a constriction in a sample chamber. FIG. 9A, shows a transmitted light image of the microparticles trapped in a sample chamber. FIG. 9B, is a close-up image of four microparticles shown in FIG. 9A. FIGS. 9C-E show that the four types of microparticles can be distinguished by their level of coding red, blue, and green fluorescence. On each microparticle, the green intensity indicates the amount of cytokine captured on that microparticle. For example, a higher concentration of IL-6 was detected compared to IL-1β. In this sample, IL-1β is not present.

Figure 10:
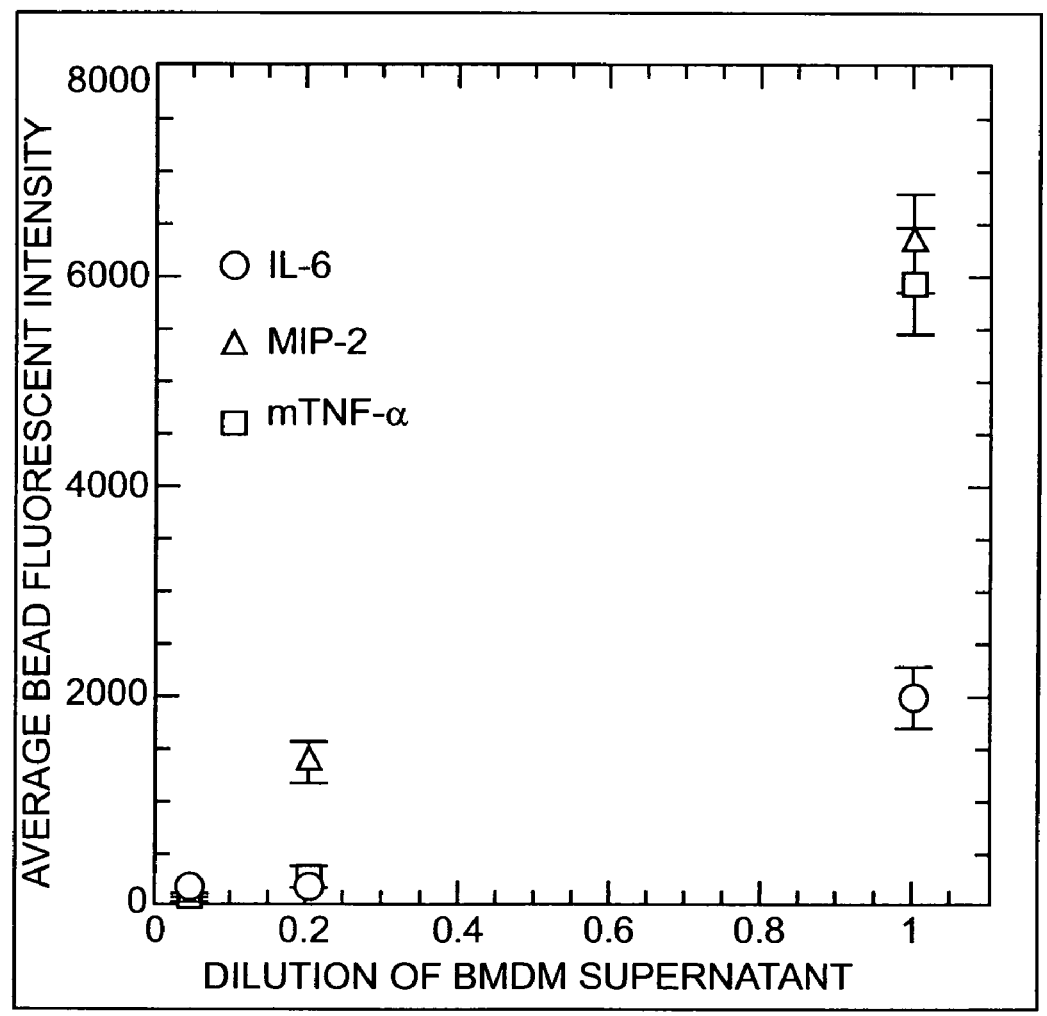

FIG. 10 shows the results of a multiplex assay for measuring the concentration of three proteins detected in the supernatant of a bone-marrow-derived macrophage culture stimulated for 4 hours with lipopolysaccharide (LPS). The original supernatant, as well 1:5 and 1:20 dilutions, were introduced into three separate sample inputs in order to measure the linearity of detection.

DEFINITIONS

Throughout the specification and claims, including the detailed description below, the following definitions apply.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Other than in the operating examples, or where otherwise indicated, all numbers expressing quantities used in the specification and claims are to be understood as being modified in all instances by the term "about." Accordingly, unless indicated to the contrary, the numerical parameters set forth in the present specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The term "analyte" as used herein refers to any material in a sample that can be detected, quantified, or otherwise analyzed in an assay, either directly, or indirectly through the addition of other reagents.

Examples of analytes include biological target molecules, such as proteins, nucleic acids, carbohydrates, lipids, antibodies (monoclonal or polyclonal), antigens, oligonucleotides, specific receptor proteins, ligands, anti-dyes, anti-hapten antibodies, biotin-avidin detection reagents, fluorescent proteins, and the like.

The term "analyzing" herein refers to detecting the presence, qualitatively identifying, or quantitatively measuring the amount, concentration, or activity of analytes.

The term "sample" as used herein refers to a solution comprising at least one analyte. Examples of samples include biological fluids such as serum, plasma, urine, tear, cells, cell mixtures, cell culture supernatants, or cell lysates containing one or more biological target molecules. Furthermore, samples can also comprise any conditioning reagents (e.g., permeablizing reagents) needed to render analytes soluble and accessible to detection and quantification. Such conditioning reagents may be added to the sample at any time before or after the sample is added to the devices of the present invention.

The terms "microfluidics," refer to a set of technologies that control the flow of nanoliter and picoliter amounts of fluids in miniaturized systems.

The term "microfluidic device" as used herein refers to a device consisting of one or more microfluidic channels designed to carry, store, or analyze fluid or suspended particles, typically involving sub-microliter volumes.

The term "microfluidic system" as used herein refers to a microfluidic device and its associated control apparatus, including electronics, pneumatic valves, detection optics, heating elements, etc.

The term "microfluidic plumbing" as used herein refers to the fluid handling elements of a microfluidic device including channels, chambers, valves, etc.

The term "micro-scale sensing element" as used herein refers to a solid element by means of which an analyte is detected. A typical example of a micro-scale sensing element is a microparticle. Unless the context indicates otherwise, whenever more than one micro-scale sensing element is referenced in this application, each such micro-scale sensing element can detect the same or a different analyte as the rest of the referenced micro-scale sensing elements.

The terms "microparticles", "microspheres," "beads," "microscale particles", or "nanoparticles" of the invention as used herein refer to solid particles less than 100 µm in diameter that are stable (do not dissolve) and in the solvent of interest and that have at least one substrate on the surface of each particle. It should be understood that, throughout this application and unless the context indicates otherwise, each embodiment of the invention that has been exemplified in terms of microparticles, can also be carried out in terms of other known micro-scale sensing elements.

Examples of microparticles include molecular probes, fluorescent particles, optically encoded particles, chemically functionalized particles, fluorophores, micro- and nanospheres, bio-bar code particles, magnetic particles, antibody-labeled particles, plastic or glass microspheres, particles that are distinguished by some imbedded fluorescent or luminescent material, and the like. Specific examples of microparticles or nanoparticles include antibody-coated microspheres, color-coded microspheres (e.g., from Luminex Corporation), Cytometric Bead Array (e.g., from BD Biosciences); Qbead™ and Qdot® quantum dot-encoded microspheres (e.g., from QuantumDot); particles that are distinguished by their size, shape, or light scattering properties such as metallic nanoparticles, semiconducting nanowires, aluminum-etched nanowires, shape-modulated gold wires, and the like. See, for example, Finkel et al., *Anal. Chem.* 76(19):352A-359A (2004); Han et al., *Nat. Biotechnology* 19:631-635 (2001); Nicewarner-Peña et al., *Science* 294:137-141 (2001); Matthias et al., *Advanced Materials* 14:1618-1621 (2002).

The term "reagent" as used herein refers to a compound or solution used in carrying out a reaction, such as detecting an analyte. Examples of reagents include blocking solutions, hybridization solutions, wash buffers, detection antibodies, secondary antibodies, fluorescent dyes, functionalized microparticles, and the like.

The term "assay" as used herein refers to a procedure used for the quantitative or qualitative analysis of an analyte. Examples of assays include cell-based assays, immunological assays, antigen-antibody assays, enzyme-linked immunosorbent assays, chemotaxis assays, functional assays, oligonucleotide hybridization assays, gene expression profiling, small molecule screenings, and the like.

The term "nanoliter volume" as used herein refers to volumes of less than 0.1 microliters.

The term "microfluidic channel" as used herein refers to a flow path in a microfluidic device through which a fluid can flow.

The term "flow layer" as used herein refers to an independent layer of the microfluidic device containing a plurality of channels that are used to handle all fluids associated with the analysis of a sample.

The term "control layer" as used herein refers to an independent layer of the microfluidic device containing a plurality of channels that are used to control the flow of fluids in the flow layer.

The term "flow channel" as used herein refers to a microfluidic channel present in the flow layer.

The term "control channel" as used herein refers to a microfluidic channel present in the control layer.

The term "sample chamber" as used herein refers to a fluidically-isolatable flow channel, or series of flow channels, containing a sample.

The term "detection chamber" as used herein refers to a fluidically-isolatable section of a flow channel or series of flow channels, containing micro-scale sensing elements, or any other substrate used to analyze samples. Therefore, when a sample chamber contains micro-scale sensing elements, such a sample chamber is also a detection chamber.

The term "fluidically-isolatable section" as used herein refers to a section of a microfluidic device that can contain a distinct volume of fluid, which can be isolated from contact with other fluid portions of the device.

The term "fluidically-isolatable chamber" as used herein refers to a chamber of a microfluidic device that can contain a distinct volume of fluid, which can be isolated from contact with other fluid portions of the device. The term "chamber" in this context applies to any chamber in a microfluidic device, such as sample chambers and detection chambers.

The term "plurality of fluidically-isolatable sample chambers" as used herein refers to the maximum number of fluidically-isolatable sample chambers that can be present in a given microfluidic device. In general, the meaning of the term "plurality of items X" as used herein depends on the context in which it is used, and refers to the maximum number of items X that can be present in that context.

The term "partitionable chamber" as used herein refers to a chamber that can be subdivided into smaller compartments by control channels overlaying the chamber.

The term "constriction" as used herein refers to an element that reduces the original cross-sectional area of a flow channel. Such element can be made out of the same or different material as the flow channel. Microfluidic channels in a typical microfluidic device are 15 microns high and 100 microns wide. Constrictions are dimensioned so that they allow the passage of fluid but retain other materials, such as micro-scale sensing elements or cells. For example, typical constrictions of the invention are 4 microns high and 40 microns wide, and therefore, can retain particles larger than 4 microns in diameter. Constrictions are not governed by fluid flow in the control layer.

DETAILED DESCRIPTION OF THE INVENTION

The present invention is generally directed to microfluidic systems, including devices and methods, useful for simultaneously analyzing multiple analytes from each of a plurality of distinct nanoliter-volume samples.

The present invention provides devices and methods for performing one or more assays, associated with one or more samples, for the detection of one or more analytes in a single sample chamber within a single microfluidic device. The microfluidic device may comprise a plurality of pathways, which may be interconnected or independent of one another, thus providing the ability to run parallel samples or complex assays.

In an embodiment, the present invention is directed to a microfluidic device comprising: one or more sample chambers; wherein at least one of the one or more sample chambers comprises a sample and one or more micro-scale sensing elements; wherein the volume of each sample is a nanoliter volume. In one embodiment, the micro-scale sensing elements are microparticles. In another embodiment, the device contains between 1 and 10,000 sample chambers and each of the sample chambers contains between 1 and 1000 microparticles.

In another embodiment, a microfluidic device of the invention has one or more flow layers and one or more control layers. In another embodiment, the microfluidic device contains between 1 and 100 sample chambers and each of the sample chambers contains between 1 and 50 microparticles. One of the advantages of the devices of the invention is that they provide a suitable enclosed environment that eliminates the possibility for spilling, contamination, or cross-contamination of samples.

In another embodiment, the invention comprises a microfluidic device, comprising: one or more flow layers; and one or more sample chambers; wherein at least one of the one or more sample chambers comprises a sample and one or more micro-scale sensing elements; wherein each of said one or more sample chambers is part of a loop comprising flow channels, and wherein the loop allows recirculation of fluid over the micro-scale sensing elements.

In another embodiment, the invention comprises a microfluidic device, comprising: one or more flow layers; and one or more sample chambers; wherein at least one of the one or more sample chambers comprises a sample and one or more micro-scale sensing elements; wherein the sample and the one or more micro-scale sensing elements are introduced into the sample chamber via different flow channels.

In another embodiment, the invention comprises a microfluidic device, comprising: one or more flow layers; and ten or more sample chambers; wherein at least one of the ten or more sample chambers comprises a sample and one or more micro-scale sensing elements; and wherein each sample volume is a nanoliter volume.

In another embodiment, the invention comprises a microfluidic device, comprising: one or more flow layers; one or more control layers; and one or more sample chambers; wherein at least one of the one or more sample chambers comprises a sample and one or more micro-scale sensing elements; and wherein the one or more micro-scale sensing elements are trapped in each of the one or more sample chambers by a method other than partially closing a flow channel via a control channel.

Microfluidic Devices

The microfluidic devices of the invention comprise a plumbing network of channels that allows the efficient handling of all fluids associated with the analysis of a sample. The microfluidic plumbing network and valves may be formed, for example, by creating a multilayer microfluidic device having one or more flow layers and one or more control layers. The one or more flow layers can have one or more flow channels, and the one or more control layers can have one or more control channels that cross one or more of the flow channels. The flow channels are fluidically independent from the control channels. The flow channels can comprise a plurality of sample chambers and a plurality of detection chambers.

The chambers can be formed by activating, or displacing the appropriate control channel that crosses the flow channel. In this way, the control channels operate as pressure-actuated valves. See, e.g., Quake et al., *Sience* 290:1536-1540 (2000); and Thorsen et al., *Science* 298:580-584 (2002). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al., *Science* 288: 113-116 (2000), WO 02/43615, and WO 01/01025. The control channels are manipulated by controlling the pressure within each channel using an external pump or a solenoid-controlled pressure source. See, for example, Unger et al., *Science* 288:113-116 (2000); Liu, J et al., *Electrophoresis* 23:1531-1536 (2002); Quake et al., *Science* 290:1536-1540 (2000); and WO 01/01025. The control channels can be used to isolate or partition the sample chambers within the microfluidic device. Because the control channels are independently addressable, the control channels can also be used to provide more complex flow control, such as peristaltic pumping or mixing. The devices provided herein incorporate such pumps and valves to isolate selectively a site at which reagents are allowed to react (e.g., the detection chamber where optically distinguishable microparticles are trapped). These reaction sites can be located at any of a number of different locations within the device.

Figures 3D, 3E, 3F:
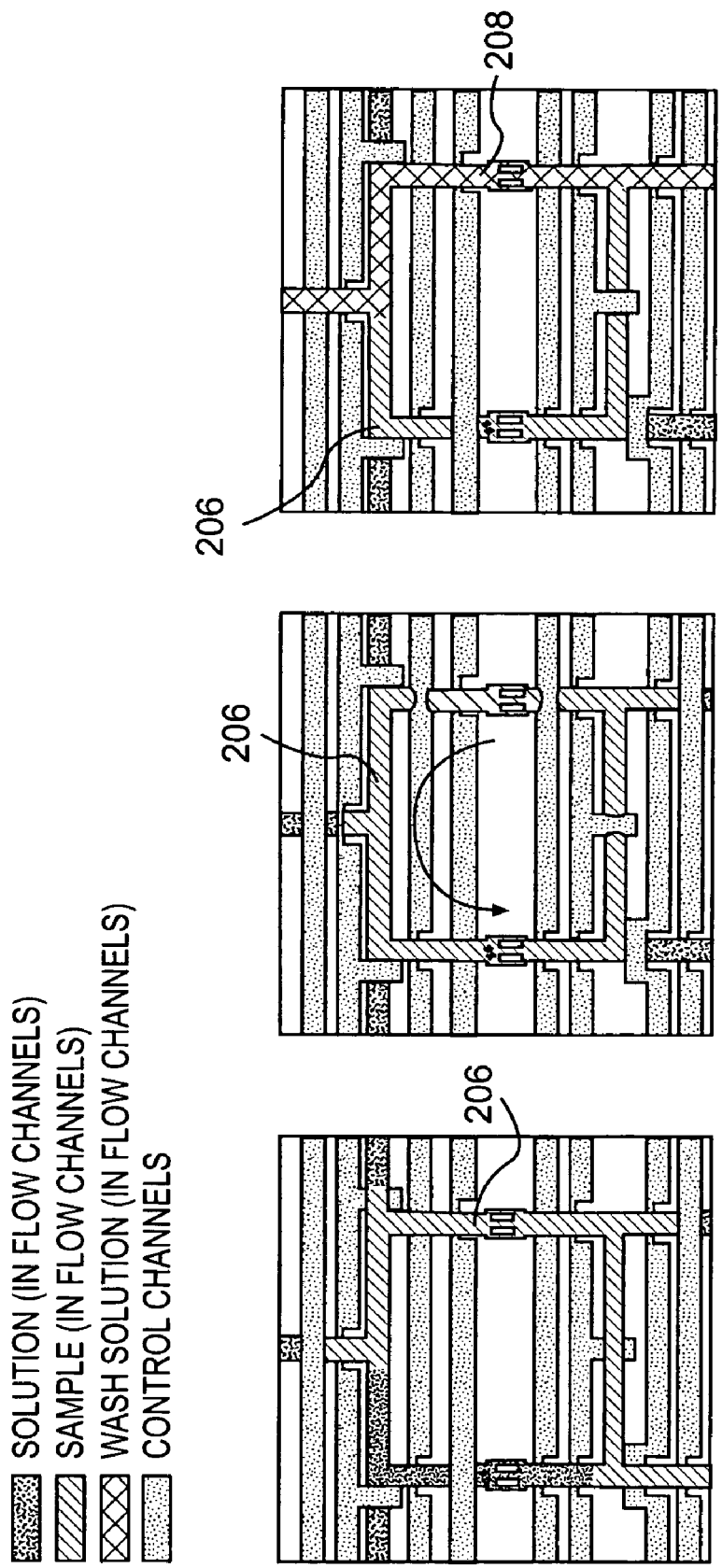
Figure 4:
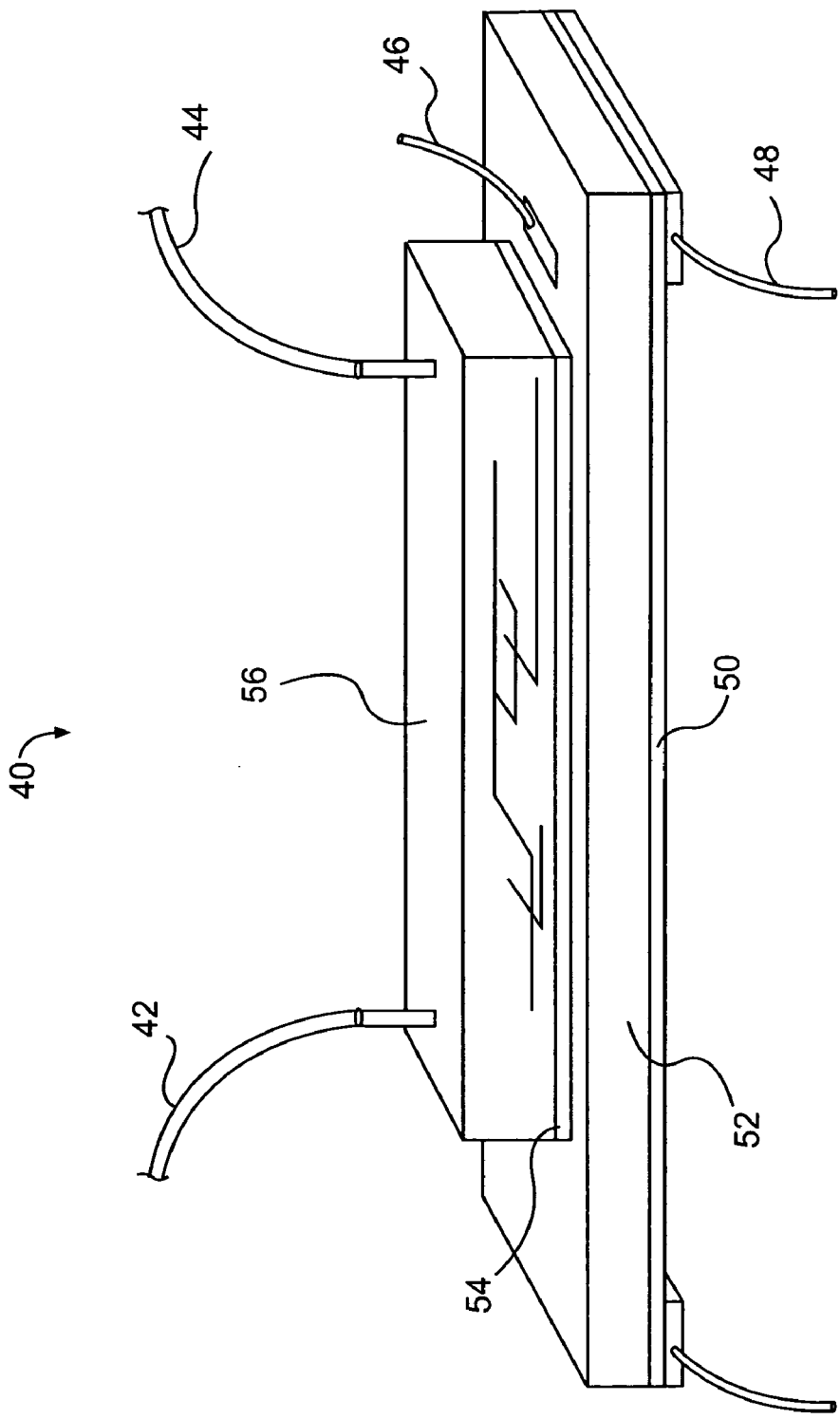
FIG. 4 is a schematic representation depicting a microfluidic system 40 including the multilayer polydimethylsiloxane (PDMS) device architecture of the microfluidic device. Flow layer connections 42 (with operating pressure of 0-5 psi) connect flow channels within the flow layer 54 to fluid reservoirs (not shown). In this example, the flow layer 54 is 35 µm thick using 20:1 PDMS.

The control channels may also be used to mix the sample and/or place the sample in contact with microparticles within the flow channels or sample chambers by partitioning the flow channel or chamber with control channels at either end of the "mixing chamber" and activating and deactivating at least one control channel between the ends of the mixing chamber. In an embodiment of the present invention, a set of control channels can be manipulated to function as a peristaltic pump by sequentially activating at least three control channels to recirculate fluid within the flow channels in a predetermined direction. As shown in FIG. 3, recirculation may be achieved using a microfluidic plumbing network comprising a plurality of control channels that are pressurized in a predeteremined sequence such that the reagents are recirculated through the flow channels. Because of recirculation, the contacting of the biological target molecules with the microparticles is improved. A thorough interaction of the samples with the microparticles as the result of recirculation increases the capture efficiency and detection sensitivity. Other methods for efficiently contacting the biological samples with the microparticles include prolonged diffusive mixing (e.g., see FIG. 6A) or flowing a well-defined volume of sample back and forth over functionalized microparticles. All of these schemes can be implemented with the devices of the present invention. The same methods used to mix samples can be used to place any reagent in contact with a sample, or with microparticles within a microfluidic device.

The microfluidic devices of the invention may also comprise a fluid multiplexer through which samples, microparticles, and other reagents, such as blocking solutions, detection beads, secondary antibodies, wash buffers, etc., are loaded. See, for example, by Thorsen T. et al., *Science* 298: 580 (2002).

Because the devices are typically made of elastomeric materials that are relatively optically transparent, detection chambers can be readily monitored using a variety of different detection systems at essentially any location on the microfluidic device. Most typically, however, detection occurs at the reaction site itself (e.g., the detection chamber where optically distinguishable microparticles are trapped). The fact that the device is manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

The microfluidic devices disclosed herein are typically constructed at least in part from elastomeric materials and constructed by single and multilayer soft lithography (MSL) techniques and/or sacrificial-layer encapsulation methods as described, for example, in Unger et al., *Science* 288:113-116 (2000). Other techniques useful in the fabrication of microfluidic devices include: photolithography and chemical etching, as described, for example, in Nguyen et al., *Fundamentals and Applications of Microfluidics* Artech House (2002); laser cut laminates; and PDMS based fabrication. Detailed individual steps for fabricating a PDMS microfluidic device can be found, for example, in Unger et al., *Science* 288:113-116 (2000); Quake et al., *Science* 290:1536-1540 (2000); Thorsen et al., *Science* 298:580-584 (2002); and PCT Publication WO 01/01025. Examples of PDMS elastomers include Dow Corning's Sylgard® 182, 184, or 186 Silicone Elastomer (Dow Corning), Silicone RTV 615 (General Electric), and the like.

The microfluidic devices of the present invention are typically fixed to a support (e.g., a glass slide or supports of other suitable materials). If the device is to be utilized in temperature-controlled reactions (e.g., at 37° C., 4° C., or temperature cycling, depending on the temperature conditions suitable for the assay of interest), then the elastomeric device can be placed on a temperature control plate, for example, to control the temperature at various sections of the device. An alternative temperature control scheme involves electrical heating via a resistive metal coating applied to the slide surface. In one embodiment of the invention, appropriate reagents (e.g., blocking solution, wash buffer, etc.) useful in pre-treating the active area of the chip, including the recirculating chambers, are introduced into a microfliuidic device of the invention. For example, a solution of blocking reagent can be used to coat the walls of PDMS channels and prevent non-specific binding of analytes and/or any other assay reagents.

In another embodiment, one or more flow channels can have one or more constrictions. Such constrictions are dimensioned so that they allow the passage of fluid through the flow channel, but impede the passage of other materials whose retention is desired, such as micro-scale sensing elements (e.g., microparticles) or cells. See, for example, FIGS. 2 and 3. For instance, when a suspension of microparticles is introduced into a flow channel comprising a constriction, the microparticles are pushed up against the constrictions and are trapped in place, but allow flow of fluid around them. In this manner, microparticles can be distributed and retained in one or more different sections of one or more different flow channels throughout the flow layer of the microfluidic device. In another embodiment of the invention, the microparticles are trapped by partial closing of valves (i.e., using control channels) in the control layer. These valve sets might operate at different pressures, or at identical pressures, and can vary the cross-sectional area of a flow channel in order to control the degree of constriction obtained. Materials can be retained in a flow channel by using "sieves", which may be dynamic and under the control of valves in the control layer. For example, when pressurized, small footprint valves in the control layer can partially restrict the flow in the corresponding flow layer, trapping the desired materials.

The present invention also contemplates the use of other methods to trap microparticles in place in the sample chambers, including the use of dielectrophoresis; optical tweezers, which can be used to trap and/or manipulate individual refractive particles under illumination, see also Ashkin A. et al., "Observation of a single-beam gradient force optical trap for dielectric particles", Optics letters 11:288-290 (1986); magnets, to trap magnetic beads or microparticles made out of metals; micro wells, which represent a micro-region (within the sample chamber) having an upper surface with a pattern of micro-orifices capable of trapping microparticles; and gels, which can be made of any kind of gel media that can trap microparticles in a sample chamber but that allows the passage of biological samples through the chamber and/or over the microparticles (e.g., agarose or acrylamide).

To measure the abundance, level, activity or presence of one or more biological target molecules, biological samples comprising said biological target molecules are introduced into the microfluidic device and are manipulated so that each biological sample contacts a separate sub-set of microparticles that may be sensitive to the same or different analytes.

Another embodiment of the invention comprises an integrated microfluidic system, which comprises a microfluidic device of the invention; a detection system; a data acquisition control system; and a microfluidic control system. A detection system is used to detect a signal within a microfluidic device of the invention and comprises one or more detection methods, or a combination of one or more detection methods, including microfluidic flow cytometry, microscopy, spectroscopy, Surface Plasmon Resonance spectroscopy (SPR), light scattering, fluorescence, absorption, enzyme-linked amplification, and the like. A data acquisition control system is used, inter alia, to acquire, control, manipulate, and/or store data produced by or obtained from the microfluidic device, including data measured by the detection system. A typical data acquisition control system comprises a computer and suitable computer software capable of acquiring, controlling, manipulating, and/or storing data relevant to an experiment carried out using a microfluidic device of the invention. A microfluidic control system is used to control fluid flow in the control and/or flow layers and may comprise external pressure and pumping systems, necessary valves, piping, tubing, etc., as well as a computer and computer software capable of controlling said systems and devices. The data acquisition control system and the microfluidic control system may comprise the same or different computer and/or computer software.

Micro-scale Sensing Elements

In multiplexing assays, microparticles are the most common type of micro-scale sensing element. Microparticles comprise a substrate by means of which an analyte can be analyzed. Currently, there are microparticles available on the market attached to a wide variety of substrates, such as, for example oligonucleotides, proteins, antibodies, or drugs. For instance, there are microparticles that detect cytokines, single nucleotide polymorphisms, phosphoproteins, proteins, and other target analytes. The microfluidic devices and methods of the invention contemplate the analysis of any analyte for which microparticles having the appropriate substrate are available, either commercially or on a custom-made basis.

In one embodiment of the invention, microparticles with different substrates attached to their surface are introduced into each sample chamber using the microfluidic plumbing network of channels and valves. In one embodiment of the invention, the sample and the microparticles are introduced into the microfluidic device using the same set of flow channels. In another embodiment, the flow channels used to introduce the sample are different from the flow channels used to introduce the microparticles. These microparticles are sized such that they can be transported through a flow channel and so that several of them can fit inside a single sample or detection chamber. Each type of microparticle is able to bind, and therefore analyze, a different target analyte. Therefore, when different types of microparticles are present in the same sample chamber, such collection of microparticles is able to analyze more than one analyte. The unique signatures of each microparticle allow one to distinguish which of the targets have bound to the microparticle. In the case of Luminex microparticles, for example, these signatures are the distinct spectral markers produced by a ratio of a red dye and an infrared fluorescent dye. The Luminex system currently provides 100 unique microparticles, which according to one embodiment of current invention, allow one to perform 100 different assays (each for a different analyte) in a single sample chamber. Other optically distinguishable microscale particle systems may have between 1,000 and 10,000 microparticles since other companies may use various microparticle sizes, fluorescent intensities, or dyes to differentiate their microparticles. For example, metallic microscale particle systems may have more than 100,000 optically distinguishable particles.

In a particular embodiment of the invention, the microfluidic device comprises between 1 and 10,000 fluidically-isolatable sample chambers; wherein each of said one or more sample chambers contains between 1 and 1,000 different types of microparticles, each type of microparticle being capable of binding to a different or the same analyte. In another embodiment of the invention, the microfluidic device comprises between 1 and 1000 fluidically-isolatable sample chambers; wherein each of said one or more sample chambers contains between 1 and 100 different types of microparticles, each type of microparticle being capable of binding to a different or the same analyte. Still, in another embodiment of the invention, the microfluidic device comprises between 1 and 100 fluidically-isolatable sample chambers; wherein each of said one or more sample chambers contain between 1 and 50 different types of microparticles, each type of microparticle being capable of binding to a different or the same analyte. Other microfluidic devices of the invention may contain between 1 and 10 fluidically-isolatable sample chambers. In the microfluidic devices of the invention, a single sample chamber may contain examples of one, some, most, or all of the different types of microparticles. The optical encoding of each particle corresponds to the specific reagent or marker presented on the surface of the particle. The target molecules may include proteins, nucleic acids, carbohydrates, or various other analytes.

In another embodiment, different kinds of microparticles are used to analyze each sample in the microfluidic devices of the invention, but only one microparticle of each kind is used in each sample chamber. That is, each microparticle within each sample chamber used in this embodiment is different from any other microparticle in the same sample chamber and, therefore, each microparticle in a given sample chamber is capable of analyzing an analyte different from the analyte each other microparticle in the same sample chamber is capable of analyzing.

Each of the sub-sets of optically encoded particles can be imaged, for example by microscopy, to determine the presence or amount of biological target molecules captured by each functionalized particle. In this manner, a single microfluidic device can be used to detect or measure simultaneously the abundance of a multitude of biological target molecules in each of the individual samples delivered to each sample chamber. Additionally, the capture and detection of biological molecules on micro-scale sensing elements (e.g., microspheres) allows for a very high signal to noise in the fluorescent detection, thereby further increasing the device sensitivity.

While microparticles are the most popular format for multiplexing, there are other techniques available that allow the simultaneous detection of multiple analytes, such as microarrays, chips, and fiber optic bundles. The present invention contemplates the use of other systems different from microparticles to the extent that they can be introduced into the microfluidic device through flow channels.

Methods of the Invention

In another embodiment, the present invention provides methods for simultaneously manipulating nanoliter-scale samples and contacting these samples with functionalized microparticles. The amount or presence of the target molecule can be detected by contacting micro-scale sensing elements with the target molecules. As mentioned previously, functionalized microparticles are typically used as micro-scale sensing elements, and they can be detected and identified optically on the basis of their color, fluorescent color, size, or shape. This detection and identification can involve adding one or more labeling reagents to the collection of particles to reveal their identities by chemical interaction of the functionalized particle with the labeling reagent. See, for example, Walt, D. R., *Science* 287:451-452 (2000) and references therein.

A particular embodiment of the invention is directed to a method for analyzing one or more analytes in each of one or more nanoliter volume samples simultaneously comprising:
  optionally introducing into each of said one or more sample chambers and flow channels going into, or exiting, said one or more sample chambers, any reagents (e.g., blocking reagent, wash buffer, etc.) useful in pretreating the active area of the chip.
  introducing one or more micro-scale sensing elements, each capable of binding a different or the same analyte, into each of one or more sample chambers of the microfluidic device of the invention;
  introducing one or more samples, each comprising one or more analytes, into each of said one or more sample chambers so that each sample is placed in contact with a separate set of said one or more micro-scale sensing elements;
  optionally introducing into each of said one or more sample chambers any reagents necessary to obtain a detectable signal from said one or more same or different types of micro-scale sensing elements;
  detecting a signal from said one or more same or different types of micro-scale sensing elements; and
  interpreting the signal to obtain the desired information about said one or more analytes.

The devices and methods of the present invention can also be used for detecting nucleic acid sequences. Such methods comprise capturing microparticles derivatized with complementary oligonucleotide sequences. For example, the microfluidic devices of the present invention are sufficiently scalable to allow differently labeled populations of DNAs from a source to be competitively hybridized with reference DNAs cloned on microparticles, to provide a differential expression library. Monitoring the relative signal intensity of the different fluorescent labels on the microparticles permits quantitative analysis of the relative expression levels between the different sources. In accordance with this embodiment, derivatized microparticles such as those described in Brenner et al., PNAS 97:1665-70 (2000) can be delivered into the devices of the present invention by methods exemplified in FIGS. 2 and 3 above.

Another embodiment of the present invention provides for methods to accurately sort and categorize cells based on their cytokine profiles, or on any other measurable property. A particular embodiment contemplates providing a suitable environment for cells in the fluid channels while their cytokine profiles are being analyzed. It is further possible for cells to be automatically sorted and then recovered from the device based on their cytokine profiles. Initially, cells are kept in the sample chamber while the assay is in process. Subsequently, the plumbing network of the microfluidic device facilitates the movement of the cells to a temporary storage compartment for them to remain isolated while the detection steps are processed. The temporary sample storage compartment will provide a suitable environment for cells with no possibility of contact between them and the detection reagents. Once the detection process is completed and the results of cytokine expressions are determined, the device will automatically sort the cells from the temporary storage compartments into various collection bottles where cells are enriched for a specific cytokine expression profile. Such a method will allow for a heterogeneous population of cells to be sorted into homogeneous subpopulation of cells each having unique functional characteristics.

Time-dependent Studies

In another embodiment, the present invention provides devices and methods for detecting a time-response associated with one or more biological target molecules in a single microfluidic device. In this embodiment, the present invention provides a microfluidic device with a plurality of microfluidic channels, each so dimensioned so as to accommodate a plurality of detection chambers for time course studies. In accordance with the present invention, the pressure-actuated valves of detection partitions within each detection chamber facilitate the sequential exposure of the sample to subsets of microparticles. For example, as shown in FIG. 6, a detection chamber may have four detection partitions. Each detection partition is independently controlled by a pressure-actuated valve which controls the interaction of the sample with microparticles trapped in that partition. Sequential activation of these valves allows the sample to come into contact with four separate subsets of microparticles at four different times. In this manner, a time-response study of any biological target molecule for which a capture microparticle is available can be accomplished. The present invention also contemplates systems where sample analytes can be assayed at more than four different time points.

Detecting a time-response associated with one or more biological target molecules can yield kinetic information. For example, it is well known that cytokine protein production by a stimulated cell or population of cells is transient. For that reason, to fully characterize cytokine protein production, kinetic data associated with time-response studies is necessary. One embodiment of the present invention contemplates measuring the abundance of biological target molecules (e.g., cytokine proteins from a variety of sources, such as murine or human) associated with one or more samples at several time points as described above. This embodiment provides kinetic information on the expression or secretion of those target molecules.

The setup depicted in FIG. 6 can also be used for assaying the intracellular and secreted analytes from one or more cells, in a single microfluidic device. As shown in FIG. 6A, a single prokaryotic or eukaryotic cell can be housed in a microfluidic channel of the device in the present invention and the secretion of biological target molecules (e.g., cytokines, chemokines, etc) from the cell can be assayed as they are produced by the cell. In another instance, a single cell in a microfluidic channel of the present invention can be localized in a sample chamber where it can be permeabilized by existing permeabilizing protocols (e.g., detergent-based methods or alcohol-based methods; see Current Protocols In Molecular Biology, John Wiley & Sons, Inc. (2005)). Upon permeabilization, the secretion of intracellular analytes can be assayed as described above. Furthermore, as mentioned previously, the secretion of biological target molecules from the cells can be assayed at several time points and the kinetics of abundance of these molecules can be captured as a function of time.

Another example of the utility of the invention includes the quantitative characterization of the abundance of various analytes in blood or plasma samples. The microfluidic devices of the present invention are sufficiently scalable to allow for assaying of hundreds of blood analytes in parallel by using only a minute amount of sample. The benefit of using such a device is the relatively low total amount of sample required, which eliminates the need for drawing milliliters of blood from patients. Rather, only a few micro liters of blood will be sufficient to run hundreds of tests simultaneously in parallel. At the moment, latest blood glucose meters draw about 1.5 µL of blood to test only the glucose levels in blood. With that amount of blood, the device in the present invention can measure the levels of up to several hundreds of analytes in blood. Such a test could encompass an array of informative cytokines for disease diagnosis purposes.

Other uses of the devices and methods of the invention include, for example, protein detection and quantification (e.g., cytokines, chemokines, enzymes, and the like, using, for example, immunology-based assays, such as ELISA); nucleic acid detection and quantification (including, for example, detection of nucleotide sequence mutations or deletions); detection of disease biomarkers (e.g., cancer biomarkers); detection of plasma components (e.g., inorganic, organic, or biological molecules such as carbohydrates, peptides, and the like); and analysis of multiple closely-related chemical compounds in combinatorial chemistry; among others.

The following examples are presented to further illustrate certain aspects of the devices and methods disclosed herein. However, these examples are not to be considered as limiting the invention.

EXAMPLE 1

Temporal Measurement of Proteins Secreted from Live Single Macrophages

An embodiment of the present invention provides methods to quantitatively characterize macrophage diversity by using a microfluidic device to measure temporal cytokine profiles from multiple, individually isolated, live macrophage cells. By isolating single macrophage cells in approximately 0.25 nL volumes, it is possible to detect various secreted proteins through the use of antibody-coated, color-coded microspheres. Moreover, the microfluidic devices of the present invention are sufficiently scalable to allow the assaying of hundreds of cells, in parallel. This approach provides the added benefit of being able to quantitatively characterize cell-to-cell heterogeneity.

FIG. 6A depicts an exemplary schematic illustration of a section of a microfluidic device for performing multiplexed single-cell assays in accordance with an embodiment of the present invention. The single unit 210 of a microfluidic platform 200 can house an activated macrophage such as a cell 222. A cell 222 can be contained in an approximately 0.25 nL volume chamber 220 adjacent to four detection chambers 212, 214, 216, and 218, each of which can contain a selection of color-coded microparticles 224. After the macrophage is activated, the target secreted cytokines 226 can be captured and detected on the microparticles. Flow to the detection chambers is regulated by pressure-actuated valves 212a, 214a, 216a, and 218a that compress and seal the walls of the PDMS channels. Microparticles 228 in chamber 212 capture cytokines from an early time-point while the microparticles in chamber 214 are currently detecting secretions of the cell (note open valve). As shown in FIG. 6A, the microparticles in chambers 216 and 218 have not been exposed to the sample, but can be exposed at later points in time. Detection by immunofluorescence is accomplished using one laser (633 nm) to identify each microparticle's color-coding and a second laser (488 nm) to quantify the amount of captured cytokine. For clarity, some control lines for the microparticles and cell localization are not shown. Macrophages have a diameter of approximately 20 µm, and the microparticles 224 are about 5.6 µm in diameter. A single device, placed on a microscope slide, may house several hundred units 210.

FIG. 6B depicts a captured microparticle in a fabricated device where the dashed lines indicate the channel margins.

FIG. 6C depicts an image of a single red/blue coded microparticle, with detection of capture MIP-2 cytokine (green).

EXAMPLE 2

Fabrication of a Microfliuidic Device

I. Molds

Multi-layer PDMS microfluidic chips were manufactured as described in Unger et al., (Science 288:113-116 (2000)). Briefly, the network of channels for each layer was designed using a commercial CAD program (AutoCAD) and printed at 20,000 dpi on a transparency film [CAD Art Services, Bandon, Oreg.]. The flow and control layer molds were fabricated by photolithography using 3-inch diameter silicon wafers as substrates. The flow layer mold was fabricated by three sequential photolithographic steps, each using a different photoresist, to form the microparticle traps, flow channels, and "fluidic bus", while the control-layer mold was fabricated in a single step.

II. PDMS Chips

The molds were incubated for 5 minutes in a closed container with 0.5 ml TMCS which acted as a release agent. PDMS pre-polymer was poured (3 mm thick) onto the flow-layer mold, and spin-coated (to 35 microns thick) onto the control layer mold, and then both were baked for 1 hour at 80° C. The cured flow layer then was cut from the mold, aligned to the control layer and bonded by baking for 1 hour at 80° C. The bonded device was peeled from the mold and holes punched through the top surface to allow external connections to the microfluidic channels. PDMS pre-polymer was spin-coated onto a clean 2×3" microscope slide and baked for 40 minutes at 80° C. The bonded and punched device was placed onto this substrate and baked for 12 hours at 80° C. to seal the control layer.

III. Microparticles

Plastic microspheres functionalized with capture antibodies against murine TNF-α, MIP-2, IL-1β, and IL-6 and biotinylated secondary antibodies against each target, and purified recombinant protein standards were purchased from R&D Systems.

EXAMPLE 3

Sample Preparation

Samples derived from a supernatant of a bone-marrow-derived macrophage culture were prepared as follows:

Two million bone marrow-derived murine macrophage cells were cultured in 3 ml of media in a tissue culture incubator and activated with 30 ng/ml of lipopolysaccharide (*Salmonella minnesota* R595) for 4 hours.

The media was removed from the cells, centrifuged for 1 min at 10000×g in a microfuge to remove cellular debris. The clarified supernatant (3 μL), as well as 1:5 and 1:20 dilutions, were used in Example 4.

EXAMPLE 4

Assay Using a Microfluidic Device of the Invention

An assay in a device prepared as described in Example 2 was performed as follows. The device described, including the labeling of the various input channels and valves, is illustrated in FIGS. 8A-B.

All of the control lines were filled with water and pressurized to 24 psi. The five reagent input ports controlled by valves V9-V13 (FIG. 8A) were loaded with the following solutions and pressurized to 10 psi:

Reagent flush port—Wash buffer: 0.05% Tween 20 in PBS, pH 7.4

Block port—Blocking buffer: 1% BSA, 5% Sucrose in PBS with 0.05% azide.

Fluorescent label port—tertiary fluorescent label: Alexa-488 labeled Streptavidin diluted 1:10 (v/v) with 0.1% BSA in PBS.

Secondary antibodyport—Secondary antibodies: Biotinylated secondary antibodies against TNF-α, MIP-2, and IL-6. diluted 1:10 with 0.1% BSA in PBS.

Microparticles port—Functionalized microspheres: Plastic microspheres functionalized with capture antibodies against murine TNF-α, MIP-2, IL-6, and IL-1β diluted 1:20 (v/v) with 0.1% BSA in PBS before being loaded into the chip.

Three of the sample inputs were loaded each with a different sample to be assayed and pressurized to 10 psi. Samples were prepared as described in Example 3 from supernatant of a bone-marrow-derived macrophage culture stimulated for 4 hours with lipopolysaccharide (LPS). The original supernatant as well as 1:5 and 1:20 dilutions were used as samples in this experiment.

The sample flush input was filled with wash buffer and pressurized to 10 psi. Blocking solution (from Block port) was introduced into the active area of the chip, including the recirculating chambers, for 1 hour to coat the walls of the PDMS channels and prevent non-specific binding of protein in the sample and assay reagents. The blocking solution was subsequently flushed out with wash solution (via the reagent flush port).

Functionalized microparticles were introduced into the recirculating regions of the chip and positioned against the traps using valves V4, V5, and V6 actuated in series as a peristaltic pump (FIG. 8B), as described schematically in, for example, FIG. 2A. The recirculating loop was then flushed with wash buffer from the sample flush input and the eight samples were simultaneously introduced into their respective recirculating chambers. The peristaltic pump was activated and the sample recirculated over the trapped microspheres for 3 hours.

Both sides of the recirculating loop were then flushed with wash buffer. The Secondary antibody mixture was introduced into the recirculating loop and pumped over the microparticles for one hour. The recirculating loop was then flushed with wash buffer from the sample flush input. Fluorescent label was then introduced to the loop and pumped over the microspheres for 30 minutes.

The recirculating loop was then flushed with Wash buffer from the Sample Flush input to remove the unbound Fluorescent label. The microparticles in each recirculating chamber were imaged on a fluorescence microscope and the amount of each target protein present each sample was inferred from the fluorescent intensity on the surface of the corresponding microsphere.

FIGS. 9A-E show images of a microparticle cluster in a well from this experiment, and fluorescent detection of 3 cytokines captured on the surface of microparticles (TNF-α, MIP-2, and IL-6; microparticles in green). The microparticles in blue and the red represent the coding channels used to identify and distinguish each different microparticle. FIG. 10 shows the concentration measurement for three of the proteins detected in the supernatant of the bone-marrow-derived macrophage culture assayed.

We claim:

1. A microfluidic device comprising one or more sample chambers;
    wherein at least one of the one or more sample chambers contains at least two different microparticles; wherein the volume of each sample chamber is a nanoliter volume,
    wherein each of said at least two microparticles is functionalized with a reagent to bind a different analyte of interest;
    said device comprising a multilayer microfluidic system which comprises one or more elastic flow channels and one or more elastic control channels wherein said control channels deflect when pressurized and constrict the flow channels and wherein said flow channels comprise narrower portions to trap the microparticles in the sample chamber.

2. The microfluidic device of claim 1, wherein the at least two microparticles are trapped in each sample chamber.

3. The microfluidic device of claim 2, wherein fluid flows over the microparticles.

4. The microfluidic device of claim 3, wherein said fluid is one or more solutions each comprising one or more analytes.

5. An integrated microfluidic system comprising a microfluidic device comprising one or more sample chambers; wherein at least one of the one or more sample chambers contains at least two different microparticles; wherein the volume of each sample chamber is a nanoliter volume, wherein each of said at least two microparticles is functionalized with a reagent to bind a different analyte of interest; said device comprising a multilayer microfluidic system which comprises one or more elastic flow channels and one or more elastic control channels wherein said control channels deflect when pressurized and constrict the flow channels and wherein said flow channels comprise narrower portions to trap the microparticles in the sample chamber; a detection system; a data acquisition control system; and a microfluidic control system.

6. A method for analyzing simultaneously at least two analytes in each of one or more samples comprising:
introducing one or more samples into at least one sample chambers of an integrated microfluidic system comprising a microfluidic device comprising one or more sample chambers; wherein at least one of the one or more sample chambers contains at least two different microparticles; wherein the volume of each sample chamber is a nanoliter volume, wherein each of said at least two microparticles is functionalized with a reagent to bind a different analyte of interest; said device comprising a multilayer microfluidic system which comprises one or more elastic flow channels and one or more elastic control channels wherein said control channels deflect when pressurized and constrict the flow channels and wherein said flow channels comprise narrower portions to trap the microparticles in the sample chamber; a detection system; a data acquisition control system; and a microfluidic control system; optionally introducing into said sample chamber any reagents necessary to obtain a detectable signal from said microparticles; detecting a signal from said microparticles; and interpreting the signal to obtain the desired information about at least two analytes.

7. The microfluidic device of claim 1, wherein each microparticle is coded, wherein the coded microparticles comprise optically encoded microparticles, bio-bar coded microparticles, color-coded microparticles, quantum dot-encoded microparticles, or a combination.

8. The microfluidic device of claim 1, wherein the sample chambers in which microparticles are trapped comprise micro wells, gels, or a combination, wherein the trapped microparticles are trapped by said micro wells, gels, or combination.

9. The microfluidic device of claim 1, wherein the sample chambers in which microparticles are trapped are comprised of material that allows application of an electric field, a magnetic field, or a combination.

10. The microfluidic device of claim 1, wherein said device further comprises a supply of labels specific for each different analyte.

11. The microfluidic device of claim 1, which contains more than one sample chambers.

12. The microfluidic device of claim 11, wherein said sample chambers are arranged adjacent to each other and the control channels are configured so as to allow the fluid in the flow channels to contact the microparticles in each of the adjacent chambers in a time-dependent manner.

13. The microfluidic device of claim 12, which further contains a compartment designed to contain one or more cells connected to said sample chambers by flow channels.

14. The microfluidic device of claim 13, wherein said compartment contains one or more of said cells.

15. The microfluidic device of claim 14, wherein said cell or cells secrete more than one analyte.

16. The microfluidic device of claim 13, wherein said contact in a time-dependent manner is by opening and closing constrictions or partial closures or a combination generated by pressurizing said control channels with respect to said flow channels.

* * * * *